United States Patent
Brown et al.

(10) Patent No.: US 9,498,183 B2
(45) Date of Patent: Nov. 22, 2016

(54) PULMONARY EMBOLISM THERAPEUTIC METHODS USING THERAPEUTIC DELIVERY DEVICES AND SYSTEMS

(75) Inventors: Joe E. Brown, Lilburn, GA (US); Marja Pauliina Margolis, Coral Gables, FL (US);
(Continued)

(73) Assignee: Volcano Corporation, San Diego, CA (US)

( * ) Notice: Subject to any disclaimer, the term of this patent is extended or adjusted under 35 U.S.C. 154(b) by 152 days.

(21) Appl. No.: 13/340,583

(22) Filed: Dec. 29, 2011

(65) Prior Publication Data
US 2012/0330276 A1 Dec. 27, 2012

Related U.S. Application Data

(60) Provisional application No. 61/429,058, filed on Dec. 31, 2010.

(51) Int. Cl.
*A61M 31/00* (2006.01)
*A61B 8/12* (2006.01)
(Continued)

(52) U.S. Cl.
CPC .............. *A61B 8/12* (2013.01); *A61B 5/02007* (2013.01); *A61B 8/06* (2013.01); *A61B 8/0891* (2013.01);
(Continued)

(58) Field of Classification Search
CPC ..................... A61M 5/16831; A61M 5/16836; A61M 5/1723; A61M 2005/16863;
(Continued)

(56) References Cited

U.S. PATENT DOCUMENTS

| 4,917,085 A | 4/1990 | Smith |
| 5,135,516 A | 8/1992 | Sahatjian et al. |
| (Continued) | | |

FOREIGN PATENT DOCUMENTS

| JP | 2005507731 A | 3/2005 |
| JP | 2005245930 A | 9/2005 |
| (Continued) | | |

OTHER PUBLICATIONS

International Search Report and Written Opinion received in corresponding Patent Cooperation Treaty Application No. PCT/US2011/067755, dated Aug. 22, 2012, 9 pages.
(Continued)

*Primary Examiner* — Edelmira Bosques
*Assistant Examiner* — Nicholas Meghri
(74) *Attorney, Agent, or Firm* — Haynes and Boone, LLP

(57) ABSTRACT

Methods and devices are disclosed that, in various embodiments and permutations and combinations of inventions, diagnose and treat Pulmonary Embolism or associated symptoms. In one series of embodiments, the invention consists of methods and devices for identifying patients whose Pulmonary Embolism or associated symptoms are caused or exacerbated, at least in part, by blockages of one or more of the patient's internal pulmonary veins. In some instances, stenoses or other flow limiting structures or lesions in the patient's affected veins are identified. Further, in some instances the nature of such lesions and whether there is a significant disruption of blood pressure, or both, is ascertained. In some embodiments, methods and devices for applying one or more therapies to the blockages in the patient's pulmonary veins are provided.

20 Claims, 17 Drawing Sheets

(75) Inventors: Mary L. Gaddis, Newport Beach, CA (US)

(51) Int. Cl.

| | |
|---|---|
| *A61M 25/10* | (2013.01) |
| *A61B 5/02* | (2006.01) |
| *A61B 8/06* | (2006.01) |
| *A61B 8/08* | (2006.01) |
| *A61B 17/12* | (2006.01) |
| *A61B 18/14* | (2006.01) |
| *A61B 18/24* | (2006.01) |
| *A61B 18/00* | (2006.01) |
| *A61B 18/02* | (2006.01) |
| *A61B 17/3207* | (2006.01) |
| *A61B 8/00* | (2006.01) |
| *A61B 6/00* | (2006.01) |

(52) U.S. Cl.
CPC .......... *A61B 8/5223* (2013.01); *A61M 25/104* (2013.01); *A61B 6/507* (2013.01); *A61B 8/463* (2013.01); *A61B 8/488* (2013.01); *A61B 8/5246* (2013.01); *A61B 17/12136* (2013.01); *A61B 17/320725* (2013.01); *A61B 18/1492* (2013.01); *A61B 18/245* (2013.01); *A61B 2018/00577* (2013.01); *A61B 2018/0212* (2013.01); *A61B 2090/3735* (2016.02); *A61B 2090/3784* (2016.02); *A61M 2025/105* (2013.01); *A61M 2025/1052* (2013.01)

(58) Field of Classification Search
CPC .............................. A61M 2005/16868; A61M 2005/16872; A61M 2205/3331; A61M 2205/3344; A61M 25/10; A61M 25/1002; A61M 2025/105; A61M 2025/1086; A61M 2025/109; A61M 25/104; A61M 2025/0001; A61M 2025/0002; A61M 2025/0003; A61M 2025/1052; A61B 5/02007; A61B 6/507; A61B 8/06; A61B 8/0891; A61B 8/12; A61B 8/463; A61B 8/488; A61B 8/5223; A61B 8/5246; A61B 17/12136; A61B 17/320725; A61B 18/1492; A61B 18/245; A61B 2018/00577; A61B 2018/0212; A61B 2019/5234; A61B 2019/528
USPC ....... 604/500, 503, 505, 506, 507, 508, 509, 604/510
See application file for complete search history.

(56) References Cited

U.S. PATENT DOCUMENTS

| | | | |
|---|---|---|---|
| 5,267,954 A | 12/1993 | Nita | |
| 5,336,178 A | 8/1994 | Kaplan et al. | |
| 5,419,777 A | 5/1995 | Hofling | |
| 5,421,338 A | 6/1995 | Crowley et al. | |
| 5,427,118 A | 6/1995 | Nita et al. | |
| 5,476,450 A | 12/1995 | Ruggio | |
| 5,507,761 A | 4/1996 | Duer | |
| 5,512,044 A | 4/1996 | Duer | |
| 5,569,184 A | 10/1996 | Crocker et al. | |
| 5,582,178 A | 12/1996 | Yock | |
| 5,724,978 A | 3/1998 | Tenhoff | |
| 5,800,450 A | 9/1998 | Lary et al. | |
| 5,866,561 A * | 2/1999 | Ungs ................ | 514/182 |
| 5,925,055 A | 7/1999 | Adrian et al. | |
| 5,957,941 A | 9/1999 | Ream | |
| 5,967,984 A | 10/1999 | Chu et al. | |
| 6,152,878 A | 11/2000 | Nachtomy et al. | |
| 6,179,809 B1 | 1/2001 | Khairkhahan et al. | |
| 6,200,268 B1 | 3/2001 | Vince et al. | |
| 6,203,537 B1 | 3/2001 | Adrian | |
| 6,231,518 B1 | 5/2001 | Grabek et al. | |
| 6,245,066 B1 | 6/2001 | Morgan et al. | |
| 6,283,921 B1 | 9/2001 | Nix et al. | |
| 6,299,622 B1 | 10/2001 | Snow et al. | |
| 6,325,797 B1 | 12/2001 | Stewart et al. | |
| 6,354,999 B1 | 3/2002 | Dgany et al. | |
| 6,381,350 B1 | 4/2002 | Klingensmith et al. | |
| 6,471,656 B1 * | 10/2002 | Shalman et al. ............. | 600/486 |
| 6,482,171 B1 | 11/2002 | Corvi et al. | |
| 6,503,202 B1 | 1/2003 | Hossack et al. | |
| 6,535,764 B2 | 3/2003 | Imran et al. | |
| 6,592,612 B1 | 7/2003 | Samson et al. | |
| 6,613,078 B1 | 9/2003 | Barone | |
| 6,701,176 B1 | 3/2004 | Halperin et al. | |
| 6,733,474 B2 | 5/2004 | Kusleika | |
| 6,949,094 B2 | 9/2005 | Yaron | |
| 7,063,679 B2 | 6/2006 | Maguire et al. | |
| 7,074,188 B2 | 7/2006 | Nair et al. | |
| 7,175,597 B2 | 2/2007 | Vince et al. | |
| 7,179,249 B2 | 2/2007 | Steward et al. | |
| 7,215,802 B2 | 5/2007 | Klingensmith et al. | |
| 7,291,146 B2 | 11/2007 | Steinke et al. | |
| 7,292,885 B2 | 11/2007 | Scott et al. | |
| 7,359,554 B2 | 4/2008 | Klingensmith et al. | |
| 7,463,759 B2 | 12/2008 | Klingensmith et al. | |
| 7,742,795 B2 | 6/2010 | Stone et al. | |
| 7,892,188 B2 | 2/2011 | Walker et al. | |
| 8,257,265 B1 | 9/2012 | Raju et al. | |
| 8,460,333 B2 * | 6/2013 | Boyle et al. ................ | 606/192 |
| 8,529,506 B2 | 9/2013 | Brown et al. | |
| 8,882,754 B2 | 11/2014 | Brown et al. | |
| 9,066,685 B2 | 6/2015 | Brown et al. | |
| 2001/0007940 A1 | 7/2001 | Tu et al. | |
| 2001/0031981 A1 * | 10/2001 | Evans et al. ................ | 606/200 |
| 2001/0041880 A1 | 11/2001 | Brisken et al. | |
| 2003/0032936 A1 | 2/2003 | Lederman | |
| 2003/0059921 A1 | 3/2003 | Sahni et al. | |
| 2003/0092995 A1 | 5/2003 | Thompson | |
| 2003/0120142 A1 | 6/2003 | Dubuc et al. | |
| 2003/0229286 A1 | 12/2003 | Lenker | |
| 2004/0034303 A1 | 2/2004 | Korotko | |
| 2004/0044308 A1 | 3/2004 | Naimark et al. | |
| 2004/0073115 A1 | 4/2004 | Horzewski et al. | |
| 2005/0121734 A1 * | 6/2005 | Degertekin et al. .......... | 257/414 |
| 2005/0154344 A1 | 7/2005 | Chang | |
| 2005/0187541 A1 | 8/2005 | Maschke | |
| 2005/0203434 A1 | 9/2005 | Kassab | |
| 2005/0209674 A1 | 9/2005 | Kutscher et al. | |
| 2005/0222594 A1 | 10/2005 | Maschke | |
| 2005/0222596 A1 | 10/2005 | Maschke | |
| 2005/0251116 A1 | 11/2005 | Steinke et al. | |
| 2006/0111704 A1 | 5/2006 | Brenneman et al. | |
| 2006/0149308 A1 | 7/2006 | Melsheimer et al. | |
| 2006/0184048 A1 | 8/2006 | Saadat | |
| 2006/0287595 A1 | 12/2006 | Maschke | |
| 2007/0066890 A1 | 3/2007 | Maschke | |
| 2007/0106155 A1 | 5/2007 | Goodnow et al. | |
| 2007/0173919 A1 | 7/2007 | Maschke | |
| 2008/0009745 A1 | 1/2008 | Hossack et al. | |
| 2008/0058917 A1 | 3/2008 | Klingenbeck-Regn et al. | |
| 2008/0077165 A1 | 3/2008 | Murphy | |
| 2008/0119701 A1 | 5/2008 | Milner et al. | |
| 2008/0125772 A1 | 5/2008 | Stone et al. | |
| 2008/0146918 A1 | 6/2008 | Magnin et al. | |
| 2008/0262489 A1 | 10/2008 | Steinke | |
| 2008/0286327 A1 * | 11/2008 | Whitehurst et al. ......... | 424/423 |
| 2008/0287801 A1 | 11/2008 | Magnin et al. | |
| 2009/0018393 A1 | 1/2009 | Dick et al. | |
| 2009/0046295 A1 | 2/2009 | Kemp et al. | |
| 2009/0093980 A1 | 4/2009 | Kemp et al. | |
| 2009/0130021 A1 | 5/2009 | Munch et al. | |
| 2009/0182287 A1 | 7/2009 | Kassab | |
| 2009/0226413 A1 * | 9/2009 | Gurewich et al. ......... | 424/94.64 |
| 2009/0240154 A1 | 9/2009 | Meissner et al. | |
| 2009/0270731 A1 | 10/2009 | Sathyanarayana | |
| 2009/0284749 A1 | 11/2009 | Johnson et al. | |
| 2009/0323076 A1 | 12/2009 | Li et al. | |

(56) References Cited

U.S. PATENT DOCUMENTS

| | | |
|---|---|---|
| 2009/0326526 A1* | 12/2009 | Ingle et al. ............ 606/21 |
| 2010/0042121 A1 | 2/2010 | Schneider et al. |
| 2010/0081873 A1 | 4/2010 | Tanimura et al. |
| 2010/0125238 A1 | 5/2010 | Lye et al. |
| 2010/0125268 A1 | 5/2010 | Gustus et al. |
| 2010/0168714 A1 | 7/2010 | Burke et al. |
| 2010/0234698 A1 | 9/2010 | Manstrom et al. |
| 2010/0256616 A1 | 10/2010 | Katoh et al. |
| 2010/0310646 A1 | 12/2010 | Oxvig et al. |
| 2011/0004198 A1 | 1/2011 | Hoch |
| 2011/0009749 A1 | 1/2011 | Zamboni |
| 2011/0091436 A1 | 4/2011 | Orbe Lopategui et al. |
| 2011/0098564 A1 | 4/2011 | Larson et al. |
| 2011/0152744 A1 | 6/2011 | Choi et al. |
| 2012/0237503 A1 | 9/2012 | Mookerjee et al. |
| 2012/0330150 A1 | 12/2012 | Brown et al. |
| 2012/0330156 A1 | 12/2012 | Brown et al. |

FOREIGN PATENT DOCUMENTS

| | | |
|---|---|---|
| JP | 2005288165 A | 10/2005 |
| JP | 2006513731 A | 4/2006 |
| JP | 2006518638 A | 8/2006 |
| JP | 2006346468 A | 12/2006 |
| JP | 2007083054 A | 4/2007 |
| JP | 4559215 B2 | 10/2010 |
| WO | WO-03/073950 | 9/2003 |
| WO | WO-2008/137710 | 11/2008 |
| WO | WO-2009/023635 | 2/2009 |
| WO | WO-2009/107152 | 9/2009 |
| WO | WO-2010/039464 | 4/2010 |

OTHER PUBLICATIONS

Zamboni, Paolo M.D., et al, "A prospective open-label study of endovascular treatment of chronic cerebrospinal venous insufficiency," Journal of Vascular Surgery, vol. 50, No. 6, United Kingdom, 2009, 14 pages.

Spagnoli, Luigi, M.D., et al, "Role of Inflammation in Atherosclerosis," The Journal of Nuclear Medicine, vol. 48, No. 11, Rome, Italy, 2007, 17 pages.

Casserly, Ivan, M.B., et al, "Slow-Flow Phenomenon During Carotid Artery Intervention With Embolic Protection Devices," Journal of the American College of Cardiology, vol. 46, No. 8, Cleveland, United States, 2005, 7 pages.

Community Care Physicians, P.C.; Evaluation to Angioplasty in the Treatment of Chronic Cerebrospinal Venous Insufficiency in Multiple Sclerosis; ClinicalTrials.gov, Full Text, Sep. 2010, 11 pages.

European Supplemental Search Report and Opinion for Application No. 11853256.3, dated Jun. 5, 2014, 7 pages.

Japanese Patent Office, "Japanese Office Action for application No. JP 2013-547665," dated Nov. 27, 2015, 9 pages with translations.

* cited by examiner

PULMONARY EMBOLISM THERAPEUTIC METHODS USING THERAPEUTIC DELIVERY DEVICES AND SYSTEMS

CROSS-REFERENCE TO RELATED APPLICATIONS

This application claims priority to and the benefit of U.S. Provisional Patent Application No. 61/429,058, filed on Dec. 31, 2010, which is hereby incorporated by reference in its entirety.

FIELD OF INVENTION

The present disclosure relates to improved methods and devices for diagnosing and treating CCSVI (chronic cerebrospinal venous insufficiency) in patients with multiple sclerosis or other diseases that are due to or exacerbated by obstructions to blood flow and, more particularly, to methods and devices for identifying patients particularly likely to benefit from the delivery of one or more therapies to treat such patients and methods and devices for delivering such therapies.

BACKGROUND

Multiple sclerosis (MS) is an inflammatory disease of the nervous system where the fatty myelin sheaths around the axons of the brain and spinal column are damaged. As a result of this damage, the ability of nerve cells in the brain and spinal cord to communicate with each other is compromised. Almost any neurological symptom, including physical and cognitive disability, can appear with the disease. MS affects more than 350,000 people in the United States and 2.5 million worldwide. In the United States, prevalence estimates are approximately 90 per 100,000 people.

Beginning with the first description of the anatomy associated with MS by Jean-Martin Charcot in 1868, MS plaques associated with MS have been known to be centered or located around veins. Further, it has been recently shown that MS is significantly correlated with a condition called chronic cerebrospinal venous insufficiency (CCSVI). CCSVI is a condition where people have obstructed blood flow in the veins that drain the central nervous system (the brain and spinal cord) and is characterized by multiple stenoses of the principal pathways of extracranial venous drainage, the internal jugular veins (IJV) and the azygous veins (AZV), with opening of collaterals, clearly demonstrated by means of selective venography and magnetic resonance venography (MRV).

Stenosis literally means a "narrowing." Here "stenosis" or its plural "stenoses" is an abnormal narrowing of the vein that restricts blood flow. This abnormal narrowing may be the result of many things. For example, the abnormal narrowing maybe the result of a collapse of the vein, twisting of the vein, ring-like narrowings in the vein and other similar obstructions. Further, the abnormal narrowing may be the result of severe venous problems including veins that are partially closed, underdeveloped, minimally formed or almost entirely missing. In addition, an abnormal or defective valve, septum, flap or membrane may narrow, blocks or inhibit blood flow through the veins. Finally, the build up of plaque, fibrin or thrombus may cause an abnormal narrowing of the vein. With respect to MS, a consequence of a stenosis in a vein leads to problems with normal or efficient blood drainage from the brain and spine back to the heart.

Intravascular ultrasound ("IVUS") combined with a technique called virtual histology ("VH") has been particularly successful in recognizing the morphology of atherosclerotic plaque in vivo (i.e., the location and composition of plaque in the patient's body). Current developments are underway to also be able to recognize thrombus in vivo. FIG. 1 illustrates a typical intravascular imaging system 2 that uses intravascular ultrasound (IVUS). FIG. 2 illustrates a typical intravascular imaging system 2 that uses optical coherence imaging (OCT).

An example of an IVUS system is the s5i™ Imaging System sold by Volcano Corporation of San Diego, Calif. Examples of OCT imaging systems include, but are not limited to, those disclosed in U.S. Pat. No. 5,724,978 issued Mar. 10, 1998 entitled "Enhanced accuracy of three-dimensional intraluminal ultrasound (ILUS) image reconstruction" with Harm Tenhoff as inventor, US Published Patent Application Nos. 20070106155 entitled "System and method for reducing angular geometric distortion in an imaging device" with John W. Goodnow and Paul Magnin as inventors and published on May 10, 2007, 20080287801 entitled "IMAGING DEVICE IMAGING SYSTEM AND METHODS OF IMAGING" with Russell W Bowden, Tse Chen Fong, John W. Goodnow, Paul Magnin and David G. Miller and published on Nov. 20, 2008, 20090093980 entitled "REAL TIME SD-OCT WITH DISTRIBUTED ACQUISITION AND PROCESSING" with Nathanial J. Kemp, Austin Broderick McElroy and Joseph P. Piercy as inventors and published on Apr. 9, 2009, 20080119701 entitled "ANALYTE SENSOR METHOD AND APPARATUS" with Paul Castella, Nathaniel J. Kemp and Thomas E. Milner as inventors and published on May 22, 2008, 20090018393 entitled "CATHETER FOR IN VIVO IMAGING" with Larry Dick, Thomas E. Milner and Daniel D. Sims as inventors and published on Jan. 15, 2009, 20090046295 entitled "APPARATUS AND METHODS FOR UNIFORM SAMPLE CLOCKING" issued to Nathaniel J. Kemp, Roman Kuranov, Austin Broderick McElroy and Thomas E. Milner as inventors and published on Feb. 19, 2009, 20090284749 entitled "OCT Combining Probes and Integrated Systems" with Dale C. Flanders and Bartley C. Johnson as inventors and published on Nov. 19, 2009 and WIPO Published Patent Application No. WO2009023635 entitled "FORWARD-IMAGING OPTICAL COHERENCE TOMOGRAPHY (OCT) SYSTEMS AND PROBE" with Jonathan C. Condit, Kumar Karthik, Nathaniel J. Kemp, Thomas E. Milner and Xiaojing Zhang as inventors and published on Feb. 19, 2009, the collective teachings of which, in their entirety, are incorporated herein by reference.

Such imaging systems 2 may also include systems capable of identifying the makeup of the tissue and material of a patient's vasculature including so called virtual histology (VH) systems. An example of a VH system is the s5i™ Imaging System with VH capability sold by Volcano Corporation of San Diego, Calif. The imaging systems 2 may also include systems for measuring the flow of blood in a patient's vasculature. An example of such a blood flow measurement system is a color-Doppler ultrasound imaging system sold under the brand name of CHROMAFLOW® by Volcano Corporation of San Diego Calif.

In an exemplary imaging system 2, an intra-vascular ultrasound (IVUS) console 4 is electrically connected to an IVUS catheter 6 and used to acquire RF backscattered data (i.e., IVUS data) from a blood vessel. The IVUS console 4 typically includes a computing device 8 comprising a database 10 and a characterization application 12 electrically connected to the database 10 and adapted to receive IVUS data from the IVUS console 4 or directly from a transducer 14. Specifically, a transducer 14 is attached to the end of the catheter 6 and is carefully maneuvered through a patient's arteries to a point of interest along the artery. The transducer is then pulsed to acquire high-frequency sonic echoes or backscattered signals reflected from the tissue of the vascular object. Because different types and densities of tissue absorb and reflect the ultrasound pulse differently, the reflected data (i.e., IVUS data) is used to image the vascular object. In other words, the IVUS data can be used (e.g., by the IVUS console 4 or a separate computing device 8) to create an IVUS image.

An IVUS image can include light and dark regions that indicate different tissue types and/or densities. It should be appreciated that the IVUS console 4 depicted herein is not limited to any particular type of IVUS console, and includes all ultrasonic devices known to those skilled in the art (e.g., a REVOLUTION® or EAGLEEYE® IVUS catheter used in conjunction with an s5™ IVUS imaging system, all of which are sold by Volcano Corporation of San Diego, Calif.). It should further be appreciated that the IVUS catheter 6 depicted herein is not limited to any particular type of catheter, and includes all ultrasonic catheters known to those skilled in the art. Thus, for example, a catheter having a single transducer (e.g., adapted for rotation) or an array of transducers (e.g., circumferentially positioned around the catheter or longitudinally along the catheter 6) can be used with the typical imaging system 2.

It should be appreciated that the database 10 depicted herein includes, but is not limited to, RAM, cache memory, flash memory, magnetic disks, optical disks, removable disks, SCSI disks, IDE hard drives, tape drives and all other types of data storage devices (and combinations thereof, such as RAID devices) generally known to those skilled in the art. It should further be appreciated that the characterization application 12, as depicted and discussed herein, may exist as a single application or as multiple applications, locally and/or remotely stored. It should also be appreciated that the number and location of the components depicted in FIG. 1 do not limit a typical imaging system 2 but are merely provided to illustrate a typical imaging system 2. Thus, for example, a computing device 8 having a plurality of databases 10 or a remotely located characterization application 12 (either in part or in whole) or any combination of these may also be found in a typical imaging system 2.

In one embodiment of a typical imaging system 2, the characterization application 12 is adapted to receive and store characterization data (e.g., tissue type, etc.). The characterization data was determined prior to using the tissue— characterization system 2 as follows. After a specimen vascular object has been interrogated (e.g., IVUS data has been collected), a histology correlation is prepared. In other words, the specimen vascular object is dissected or cross-sectioned for histology. In one method of producing characterization data, the cross-section is previously marked, for example with a suture, so that the histology can be corresponded to a portion of the IVUS image. The cross-section is then prepared with a fixing and staining process that is well known in the art. The staining process allows a clinician to identify a tissue type(s), or a chemical(s) found within (e.g., a chemical corresponding to a particular tissue type, etc.). The identified tissue type or types is then correlated to the IVUS data as will be explained below.

Where the imaging system 2 is or includes an OCT system, the imaging system 2 typically includes a light source 20 that produces light of a desired frequency and with other desired characteristics well understood in the art that is ultimately directed from the catheter 6 to the patient's vasculature by distal optics 22. A typical OCT imaging system 2 has the light source 20 located remotely from or nearby the catheter 6. Optical fibers 24 carry the light from the light source 20 to the distal optics 22.

It should be appreciated that there may be many methods used to identify or characterize the cross-sectional object as is well understood in the art besides the method just described. Thus, any identification/characterization method generally known to those skilled in the art may be used to characterize tissue. The identified tissue type or characterization (i.e., characterization data) is then provided to the characterization application 12. In one embodiment, as shown in FIG. 1, the characterization data is provided via an input device 18 electrically connected to the computing device 8. The characterization data is preferably then stored in the database 10. It should be appreciated that the input device depicted herein includes, but is not limited to, a keyboard, a mouse, a scanner and all other data-gathering and/or data-entry devices generally known to those skilled in the art. It should further be appreciated that the term tissue type or characterization, as these terms are used herein, include, but are not limited to, fibrous tissues, fibro-lipidic tissues, calcified necrotic tissues, necrotic core, calcific tissues, collagen compositions, cholesterol, thrombus, compositional structures (e.g., the lumen, the vessel wall, the medial-adventitial boundary, etc.) and all other identifiable characteristics generally known to those skilled in the art.

In one method of characterizing tissue, the characterization application is adapted to create a histology image and to identify at least one corresponding region on an IVUS image. Specifically, digitized data is provided to the characterization application (e.g., via the input device 18), where the digitized data corresponds to the cross-sectioned vascular object. The digitized data is then used to create a histology image (i.e., a digital image or outline that substantially corresponds to the vascular object). A region of interest (ROI) on the histology image can then be identified by the operator. Preferably, the ROI is characterized by the characterization data, as previously provided, and may be the entire histology image or a portion thereof. The characterization application is then adapted to identify a corresponding region (e.g., x,y coordinates, etc.) on the IVUS image.

In view of the foregoing, what is needed is an effective method and device for assisting a healthcare provider to identify patients whose MS, or MS symptoms, are likely exacerbated if not caused, at least in part, by blockages of one or more of the patient's internal jugular veins (IJV) or azygous veins (AZV) and for those patients, methods and devices for applying one or more therapies to the blockages in the patient's IJV or AZV veins.

SUMMARY

Methods and devices are disclosed that, in various embodiments and permutations and combinations of inventions, diagnose and treat MS or MS symptoms. In one series of embodiments, the invention consists of methods and devices for identifying patients whose MS, or MS symptoms, are likely exacerbated if not caused, at least in part, by blockages of one or more of the patient's internal jugular veins (IJV) or azygous veins (AZV). In preferred embodiments of the diagnostic methods, the stenoses in the patient's affected veins are identified. In other embodiments of the present diagnostic methods, the nature of such lesions and whether there is a significant disruption of blood pressure or flow, or both, is ascertained.

In another series of embodiments, the invention consists of methods and devices for applying one or more therapies to the blockages in the patient's IJV or AZV veins. In preferred embodiments of such methods and devices, therapy is delivered to open the stenosis causing such blockages.

It is an object of this invention in one or more embodiments to identify blockages of a patient's vasculature or flow limiting or interrupting structures that have likely exacerbated if not caused, at least in part, MS, or MS symptoms, in that patient.

It is an object of this invention in one or more embodiments to treat blockages of a patient's vasculature or flow limiting or interrupting structures that have likely exacerbated if not caused, at least in part, MS, or MS symptoms, in that patient.

The invention will be described hereafter in detail with particular reference to the drawings. Throughout this description, like elements, in whatever embodiment described, refer to common elements wherever referred to and referenced by the same reference number. The characteristics, attributes, functions, interrelations ascribed to a particular element in one location apply to that element when referred to by the same reference number in another location unless specifically stated otherwise.

BRIEF DESCRIPTIONS OF THE DRAWINGS

DETAILED DESCRIPTION

Figure 1:
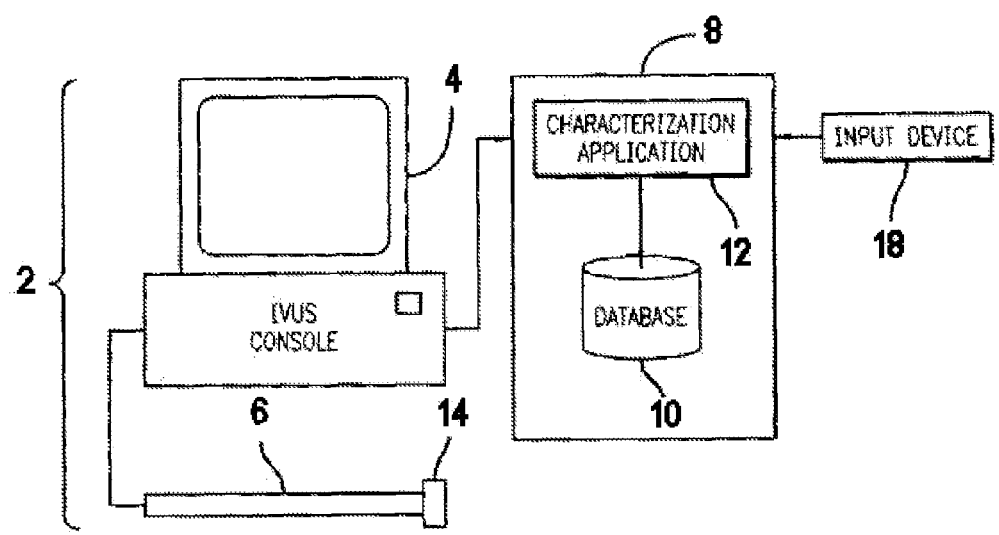
FIG. 1 is a schematic view of a typical intravascular ultrasound (IVUS) imaging system.
Figure 2:
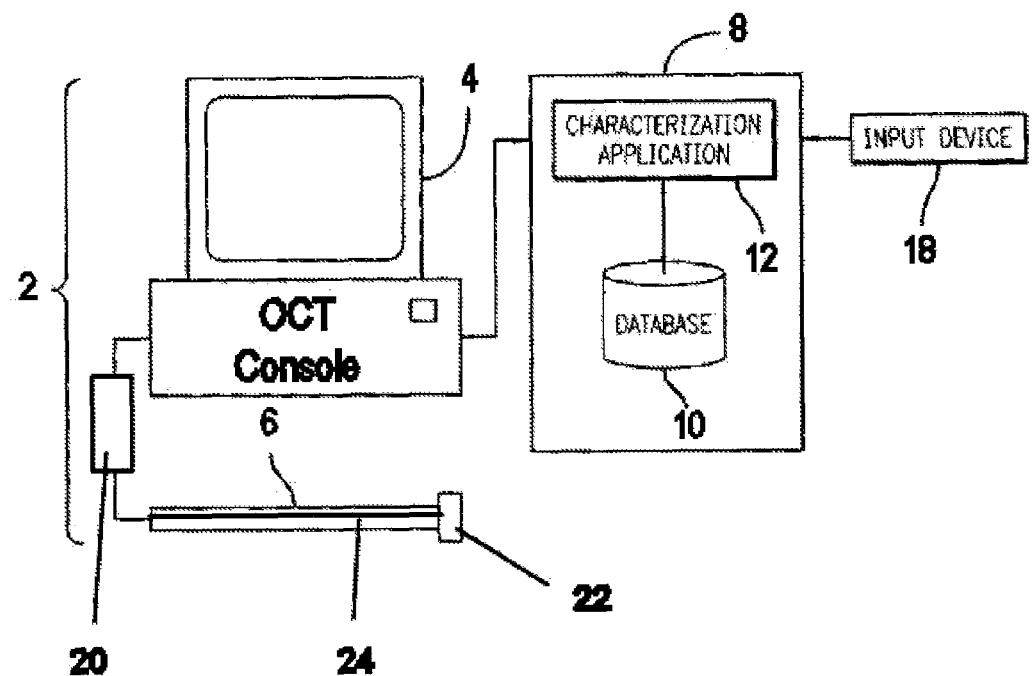
FIG. 2 is a schematic view of a typical intravascular optical coherence tomography (OCT) imaging system.

The present invention includes several embodiments. In particular, the present invention includes a Multiple Sclerosis Diagnostic Method 26, its corresponding Multiple Sclerosis Diagnostic Device 28, a Multiple Sclerosis Treatment Diagnostic and Treatment Method 30 and its corresponding Multiple Sclerosis Treatment Diagnostic and Treatment Device 32. The diagnostic method 26 and diagnostic device 28 determine whether a patient's physiology indicates that the patient has a form of MS, or MS symptoms, that are exacerbated if not caused, at least in part, by blockages or flow limiting or interrupting structures of one or more of the patient's internal jugular veins (IJV) or azygous veins (AZV). The therapeutic method 30 and therapeutic device 32 provide one or more therapies to treat the patient's MS, or MS symptoms. In embodiments of the invention, the therapeutic method 30 includes a diagnostic method 26 and, in addition, applies a therapy to treat the MS, or MS symptoms. In other embodiments of the invention, the therapeutic device 32 includes a diagnostic device 28 that, in addition, also applies a therapy to treat the MS, or MS symptoms. Examples of flow limiting or interrupting structures include, but are not limited to, physiological defects, stenoses and faulty valves.

Referring to the Figures, the diagnostic method is shown in the Figures generally referred to by the reference number 26. The diagnostic method 26, in preferred embodiments described hereafter, acts according to algorithms having the following steps, as set out in the flow charts of FIGS. 3-6.

Figure 3:
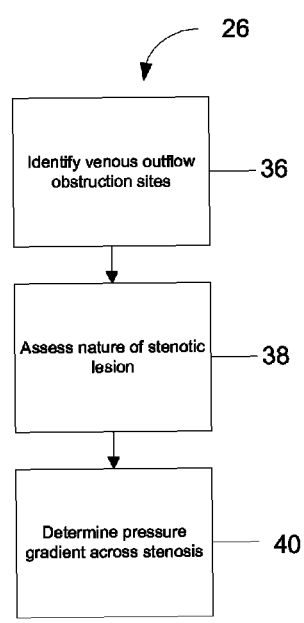
FIG. 3 is a flow chart of an embodiment of the diagnostic method of the present invention.
Figure 4:
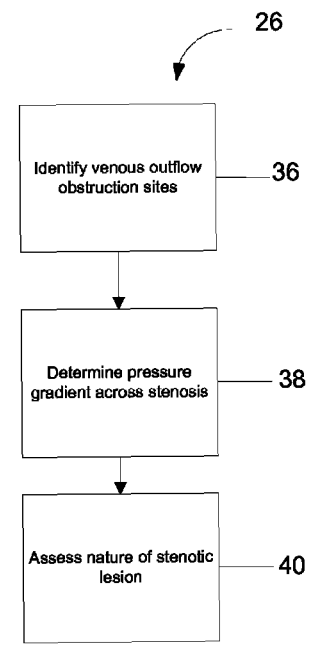
FIG. 4 is a flow chart of another embodiment of the diagnostic method of the present invention.

In the diagnostic method 26 shown in FIG. 3, the diagnostic method begins at step 36 where venous outflow obstruction sites are identified. A preferred method of identifying these obstruction sites is by sequentially accessing the AZV entry into the superior vena cava and the two Common Jugular veins by selective venography at each of these sites to confirm or exclude a significant stenosis or flow disruption. Venography, which is also called phlebography, involves taking an x-ray of the veins, a venogram, after a special dye is injected via a catheter into the vein of interest. Typically, the dye is injected constantly via a catheter. As a result, a venography is an invasive procedure.

Although venography has been a preferred method for selecting sites having significant stenosis or flow disruption, ultrasonography, including duplex ultrasonography, could also be used in the alternative or in addition to identify obstructed outflow sites.

Ultrasonography incorporates two elements:
1) Grayscale Ultrasound (e.g., from an IVUS imaging system 2) is used to visualize the structure or architecture of the vein to identify stenoses (cross-sectional narrowing of the vein);

2) Color-Doppler ultrasound imaging (e.g., from Volcano Corporation) is then used to visualize the flow or movement of a blood within the vein;

and typically presents both displays on the same screen ("duplex") to facilitate interpretation. Where ultrasonography is used, a stenosis having cross-sectional narrowing greater than about 70% is considered worthy of treatment as are blood flow velocities greater than 250 cm/sec (which also indicate a region of narrowing or resistance produced by a major stenosis). Ultrasonography can also be enhanced by tissue characterization such as the virtual histology characterization described above, for example, as part of the s5i™ Imaging System with VH capability sold by Volcano Corporation of San Diego, Calif.

Besides venography and ultrasonography, transcutaneous echography applied to an accessible section of the IJV could also be used to identify venous outflow obstruction sites and to confirm or exclude a significant stenosis or flow disruption at those sites. Further, in an embodiment of the invention, radionuclides that bind to proteins specific to fibrin, such as radionuclides bound to insulin-like growth factor (IGF) binding proteins (IGFBPs) are applied intravenously, preferably near where an obstruction is believed to be located, or orally. Then, external detectors such as gamma cameras capture and form images from the detected radiation emitted by the radionuclides that are bound to the proteins of the fibrin. This allows the areas of venous outflow obstruction caused by the buildup of thrombus to be located and to confirm or exclude a significant stenosis or flow disruption at the site. These last two methods have the desirable characteristic of being non-invasive.

In a modification of the invention above where something is bound to proteins specific to fibrin, plasmin, other plasmids or any like substance that dissolves fibrin is bound to the same IGFBP that contains the radionuclide or to an entirely different IGFBP and then delivered to the site of the fibrin as described above. The plasmin, plasmid or other substance that dissolves fibrin in whatever form may be self-activated (i.e., it is active upon delivery) or may be activated by the exposure to either a specific light frequency or by ultrasound at a specific frequency or any like energy source delivered either intravascularly or noninvasively. Where these substances are active by a specific light frequency or by ultrasound at a specific frequency, the light or ultrasound or both may be delivered via the distal optics 22 or transducer 14, respectively.

Once the venous outflow obstruction sites have been identified by whatever method, the method passes to step 38. In step 38, the nature of the stenotic lesion is assessed. This assessment is preferably accomplished by applying an imaging system 2 such as an IVUS or OCT system or a system having both IVUS and OCT or applying both IVUS and OCT imaging to suspected areas of narrowing or flow disruption to identify intraluminal abnormalities including webs, flaps, inverted or incompetent valves and membranes as well as stenoses caused by plaque or the buildup of fibrin or thrombus. Here, a significant stenosis, of whatever kind, is defined as luminal reduction greater than 50% of the normal venous diameter near the stenosis as obtained during step 36 or a significant flow disruption associated with an intraluminal abnormality noted during the IVUS or OCT imaging of this step 38. Both IVUS and OCT will provide vessel information whereby vessel circumference measurements can be made. This will allow the physician to check the lumen narrowing to determine whether such narrowing is significant as defined above (i.e., cross-sectional narrowing greater than about 70% or blood flow velocities greater than 250 cm/sec). In a preferred embodiment of the invention, software is provided on the imaging system 2 to correlate these measurements. Once IVUS or OCT or both IVUS and OCT has been used to assess the nature of the stenotic lesion, the method passes to step 40.

In step 40, the pressure gradient across the stenosis (as compared to the superior vena cava) is determined. A pressure at the superior vena cava may be compared to a pressure on an opposing side of a stenosis to arrive at a pressure gradient. The pressure gradient may be a pressure differential of a pressure distal to at least one venous outflow obstruction site of a vessel and a pressure in the superior vena cava. This pressure gradient is preferably determined using either a manometer, pressure wire or any other blood pressure measuring device if the suspected significant venous stenosis/intraluminal abnormality is confirmed by any of the methods of step 38. Examples of pressure wires are the PrimeWire PRESTIGE™ guide wire, PrimeWire® guide wire and the ComboWire® XT guide wire all made and sold by Volcano Corporation of San Diego, Calif. A pressure gradient larger than 1-2 mm Hg may indicate the presence of a significant stenosis. Information on the pressure gradient is preferably but not required to be communicated to the healthcare provider. The communication in this step 40 may take the form of a message displayed on console 4, the modifying of an image of a vascular structure displayed on the console 4 such as by appending a text or color indicator that the patient's physiology at that location on the vessel is such that the patient's pressure gradient exceeds the targeted amount, the communication of the parameter values themselves separately or by any other means well within the skill of one skilled in the art to communicate such values.

In the diagnostic method 26 described above, the listed steps 36-40 were performed in the order given. However, it is within the scope of the invention for steps 38 and 40 to be reversed. In this embodiment of the invention shown in FIG. 4, the diagnostic method 26 has the form of the steps above performed in the following sequential order:

Step 36: Identify venous outflow obstruction sites;
Step 40: Determine pressure gradient across the stenosis; and
Step 38: Assess the nature of the stenotic lesion.

Figure 5:
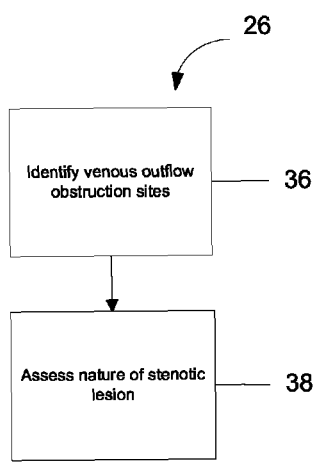
FIG. 5 is a flow chart of another embodiment of the diagnostic method of the present invention.
Figure 6:
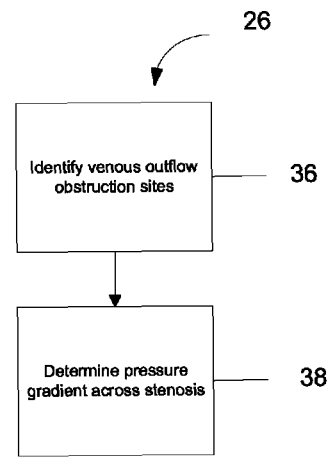
FIG. 6 is a flow chart of another embodiment of the diagnostic method of the present invention.

Further, in another embodiment of the diagnostic method 26, the method shown in FIG. 3 could be simplified so that either step 38 or step 40 is done without doing the other so that the method takes the following forms, shown in FIGS. 5 and 6, respectively, of the steps above performed in the following sequential order:

Step 36: Identify venous outflow obstruction sites; and
Step 38: Assess the nature of the stenotic lesion.
and,
Step 36: Identify venous outflow obstruction sites; and
Step 40: Determine pressure gradient across the stenosis.

As mentioned above, the diagnostic method 26 in all forms assesses whether a patient has a form of MS, or MS symptoms, that are likely amenable to treatment by a therapy that is directed to the stenosis in the patient's vein and, as a result, has diagnostic value as a diagnostic tool. This diagnostic value occurs in all the embodiments of the diagnostic method 26 described above.

Figure 7:
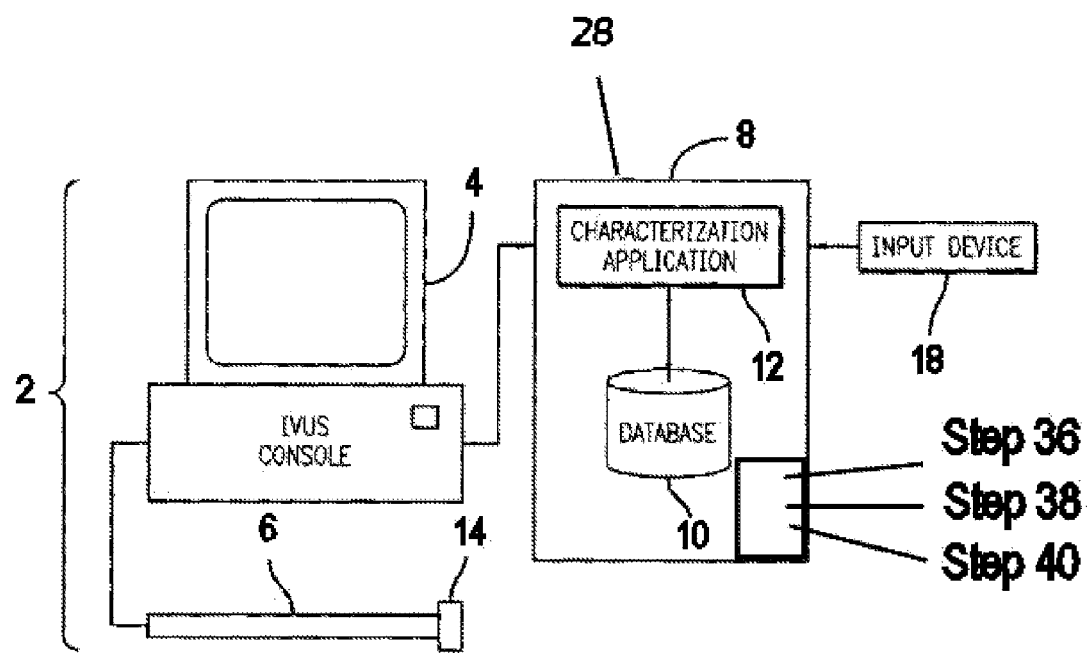
FIG. 7 is a schematic view of an embodiment of the diagnostic device of the present invention.

The diagnostic method 26 is typically run as software on a computing device 8 and thus the combination of the computing device 8 and the diagnostic methods 20, as described above, becomes the diagnostic device 28. FIG. 7 shows an embodiment of the diagnostic device 28 where the steps 36-38 are performed on the computing device 8.

Although the diagnostic device 28 is preferably operated on a computing device 8, the diagnostic device 28 may also be operated separately on any system having sufficient computing capability to perform the steps of the diagnostic method 26 and be operatively connected to the console 4, computing device 8, characterization application 12 or database 10 or any combination of these. In addition, the diagnostic device 28 may also be an application specific device or hardwired specifically to perform the functions described herein.

The diagnostic device 28, in preferred embodiments, acts according to algorithms described above in connection with the diagnostic method 26. The diagnostic device 28 may be implemented on or may be an adjunct to an imaging system 2. The imaging system 2 may take the form of an intravascular ultrasound (IVUS) imaging system 2 as described above including a console 4, IVUS catheter 6, a computing device 8 comprising a database 10 and a characterization application 12 electrically connected to the database 10 and typically run on the computing device 8. Alternately or in addition, the imaging system 2 may take the form of an optical coherence tomography (OCT) system that also includes a console 4, OCT catheter 6, a computing device 8 comprising a database 10 and a characterization application 12 electrically connected to the database 10 and typically run on the computing device 8.

Although IVUS and OCT systems singly or in combination have been described as the imaging system 2, any imaging system that obtains images of the patient's vascular may be used. Such alternate imaging systems 2 will also typically include a console 4, a catheter 6 appropriate for that imaging system 2, a computing device 8 comprising a database 10 and a characterization application 12 electrically connected to the database 10 and typically run on the computing device 8. Regardless of the imaging system 2, the diagnostic device 28 is adapted to communicate, that is both receive and transmit data and information, with the console 4 or the computing device 8.

Where it has been determined that a patient has a form of MS, or MS symptoms, that are likely amenable to treatment by a therapy that is directed to the stenosis in the patient's vein, it is also desirable to have a tool that, under the physician's control, directs a desired therapy to the stenosis. The therapeutic method 30 and its corresponding therapeutic device 32, as described hereafter, is such a tool.

Figure 8:
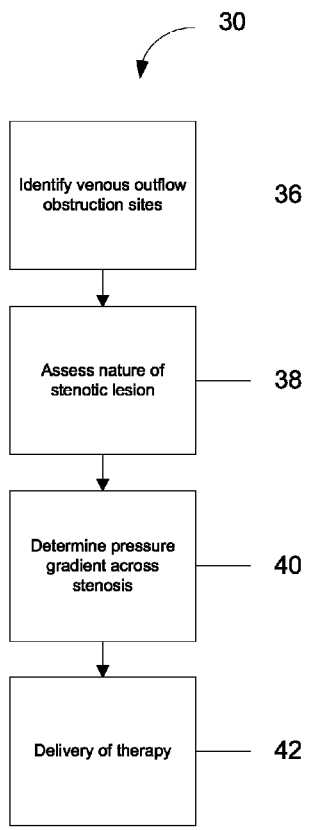
FIG. 8 is a flow chart of an embodiment of the therapeutic method of the present invention.
Figure 9:
FIG. 9 is a flow chart of an alternate embodiment of the therapeutic method of the present invention.

In one embodiment of the therapeutic method 30 shown in FIG. 8, the diagnostic method 26 is included as a diagnostic precursor to applying a desired therapy. So, the therapeutic method 30 in a preferred embodiment includes a diagnostic method 26 that operates as described above in all the variants of diagnostic method 26. In another embodiment of the therapeutic method 30 shown in FIG. 9, the therapeutic method 30 does not include a diagnostic method 26 but includes only the delivery of a therapy 42 as will be described hereafter.

In the embodiment of the therapeutic method 30 of FIG. 8 including a diagnostic method 26, after the diagnostic steps have been accomplished and it has been determined that a patient's physiology indicates that the patient has a form of MS, or MS symptoms, that are exacerbated if not caused, at least in part, by blockages of one or more of the patient's internal jugular veins (IJV) or azygous veins (AZV), the program passes to step 42. In step 42, a desired therapy is applied to treat the stenotic lesion. The therapy applied is preferably one that, as a result of the application of the therapy, produces a reduction of the stenosis such that the residual stenosis no longer is flow limiting or that a pressure gradient exceeding 1-2 mm Hg is no longer observed or both.

Figure 10:
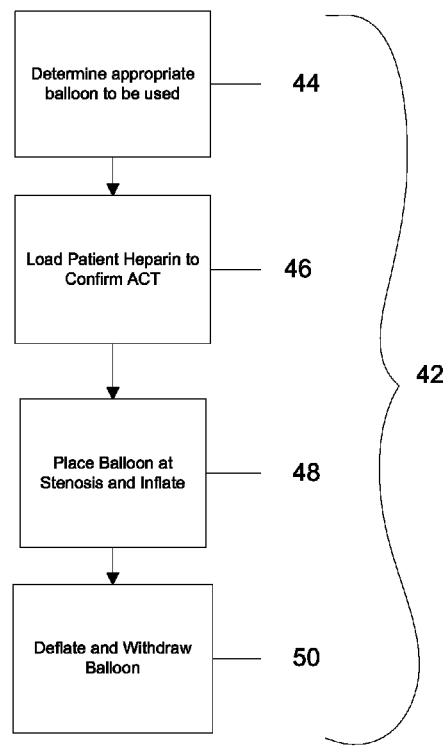
FIG. 10 is a flow chart of an embodiment of the therapy delivered as the therapeutic method of the present invention.

In one embodiment of the therapeutic method 30, a preferred therapy in step 42 is angioplasty to open or enlarge the troubling stenosis. The angioplasty may be either conventional angioplasty or angioplasty using a cutting or scoring balloon. FIG. 10 shows a flow chart of the steps involved in the therapeutic method 30 to accomplish such an angioplasty procedure. The goal of the angioplasty procedure will be to restore the venous outflow structure to where it is no longer flow limiting, flow disruption is resolved and pressure gradient is minimal.

In FIG. 10, the angioplasty therapy is begun at step 44 where the appropriate angioplasty balloon to be used is determined based on measurements previously made such as during a venogram. It is preferable but not required for the balloon to be a non-compliant balloon that will have a nominal inflated diameter of at least 80% of the normal proximal non-stenosed vein. The benefit of using a non-compliant balloon here is to obtain high pressure to increase the opportunity for compression of the obstruction.

The balloon is preferably a one piece balloon. Such a balloon may, but is not required to be, coated with or exuding a drug such as tissue plasminogen activator, urokinase, streptokinase, collagenace, hepranoids and any other fibrinolytic or direct anti-thrombin drug or drugs or antigens or both that may promote more rapid healing of a vessel.

Further, as mentioned above, the balloon may be a cutting or scoring balloon. A cutting balloon is one that has small blades that are activated (moved outward) by actuation of the balloon. The cutting blades score the fibrin of a lesion, particularly thrombus that is attached to and incorporated into the vein wall, thereby creating space that allows the rest of the fibrin to be compressed into a larger opening by the opening of the balloon. When the appropriate balloon to be used to open the stenosis has been determined, by whatever means, the program then passes to step 46. The scoring balloon is one that scores the plaque circumferentially to dilate the obstructed vessel such as the AngioSculpt Scoring Balloon Catheter made and sold by AngioScore Inc. of Fremont, Calif.

At step 46, the patient is loaded with intravenous weight based load of heparin (50-100 U/kg) to confirm an Activated Clotting Time (ACT) of at least 250 as is well understood in the art. After loading the patient with heparin to confirm ACT, the program then passes to step 48.

In step 48, the balloon is placed at the stenosis and inflated as is well understood in the art. After confirmation of the ACT, an exchange length 0.035" exchange length glide wire is advanced into the proximal vein of interest (before the obstruction) and the non-compliant balloon is placed across the stenosis. The balloon is slowly inflated, for example, with one atmosphere per 30 seconds until reaching nominal pressure (e.g., 8-12 atmospheres) to open the stenosis. The dilated balloon is left in place for a clinically significant time as is well understood in the art. After the balloon has been left in place for a clinically significant time, the method then passes to step 50.

In step 50, the balloon is deflated and withdrawn. The balloon is preferably deflated at a moderate rate (e.g., one atmosphere per 15 seconds) and then withdrawn from the patient's vascular by techniques well understood in the art.

Figure 11:
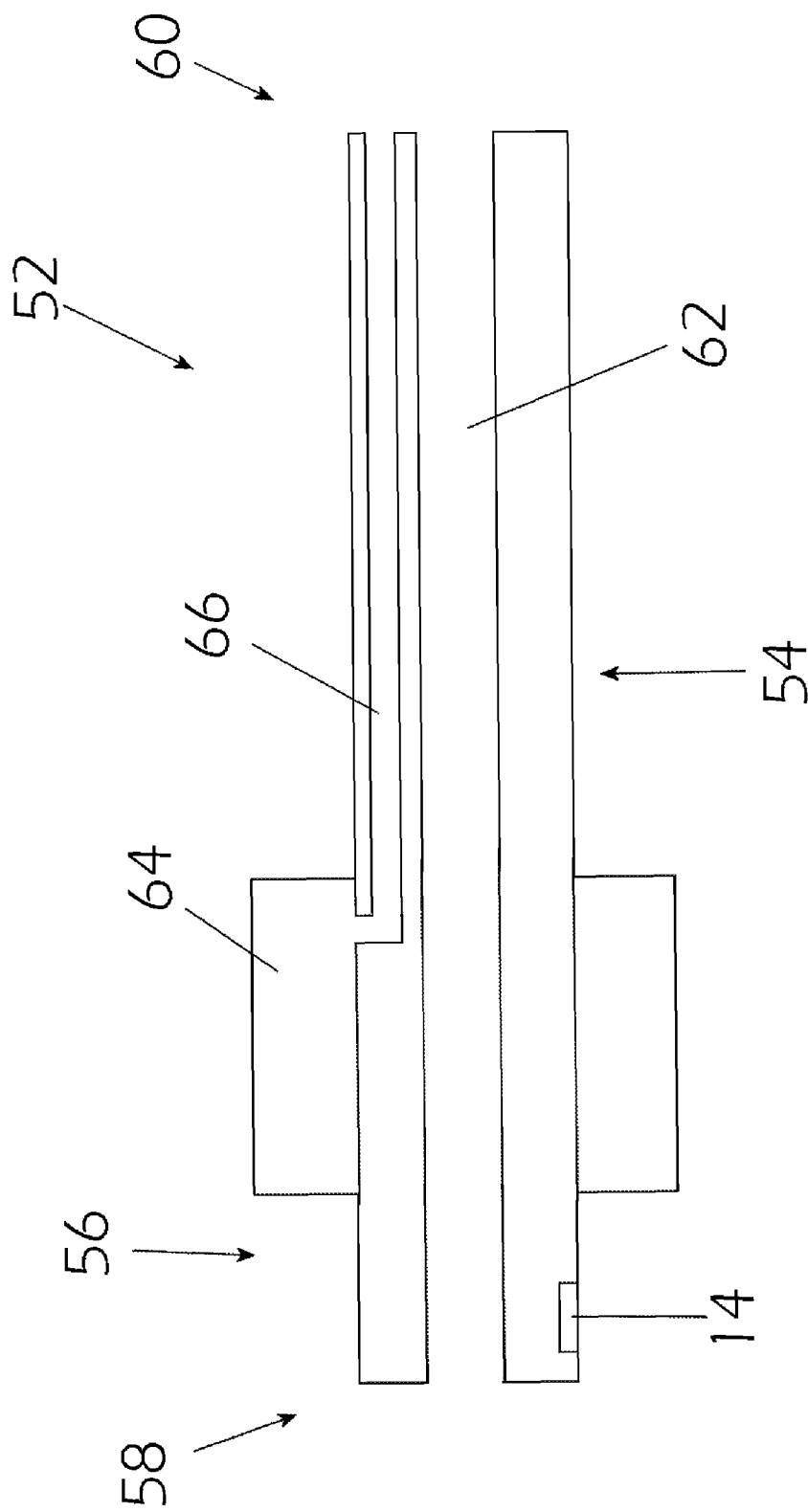
FIG. 11 is a side cross-sectional schematic view of a device of a therapy that could be applied as the therapy of the any of the therapeutic methods of the present invention.

FIG. 11 shows a device of another therapy that could be applied as the therapy in step 42. In this embodiment of the therapeutic method 30, an occlusive balloon is shown generally labeled 46. The balloon catheter 52 has a catheter body 54 with a distal end 56, an ultimate distal end 58, a proximal end 60, a central lumen 62, a balloon 64 and a balloon lumen 66. The balloon 64 is located a small distance from the ultimate distal end 58 and the central lumen 62 extends from the proximal end of the balloon catheter 52 to the ultimate distal end 58.

The balloon catheter 52 also has an imaging element or an imaging transducer 14 located at the distal end 56 of the balloon catheter 52. The imaging transducer 14 is preferably an IVUS or OCT imaging transducer that is part of an imaging system 2 such as has been described above that allows the user to identify intravascular stenoses. The imaging system 2 may also include so-called virtual histology (VH) technology to help the physician recognize and identify the morphology of tissue, particularly plaque associated with a lesion, in vivo (i.e., the location and composition of plaque in the patient's body). The following systems for detecting and characterizing plaque using IVUS with VH are disclosed in U.S. Pat. No. 6,200,268 entitled "VASCULAR PLAQUE CHARACTERIZATION" issued Mar. 13, 2001 with D. Geoffrey Vince, Barry D. Kuban and Anuja Nair as inventors, U.S. Pat. No. 6,381,350 entitled "INTRAVASCULAR ULTRASONIC ANALYSIS USING ACTIVE CONTOUR METHOD AND SYSTEM" issued Apr. 30, 2002 with Jon D. Klingensmith, D. Geoffrey Vince and Raj Shekhar as inventors, U.S. Pat. No. 7,074,188 entitled "SYSTEM AND METHOD OF CHARACTERIZING VASCULAR TISSUE" issued Jul. 11, 2006 with Anuja Nair, D. Geoffrey Vince, Jon D. Klingensmith and Barry D. Kuban as inventors, U.S. Pat. No. 7,175,597 entitled "NON-INVASIVE TISSUE CHARACTERIZATION SYSTEM AND METHOD" issued Feb. 13, 2007 with D. Geoffrey Vince, Anuja Nair and Jon D. Klingensmith as inventors, U.S. Pat. No. 7,215,802 entitled "SYSTEM AND METHOD FOR VASCULAR BORDER DETECTION" issued May 8, 2007 with Jon D. Klingensmith, Anuja Nair, Barry D. Kuban and D. Geoffrey Vince as inventors, U.S. Pat. No. 7,359,554 entitled "SYSTEM AND METHOD FOR IDENTIFYING A VASCULAR BORDER" issued Apr. 15, 2008 with Jon D. Klingensmith, D. Geoffrey Vince, Anuja Nair and Barry D. Kuban as inventors and U.S. Pat. No. 7,463,759 entitled "SYSTEM AND METHOD FOR VASCULAR BORDER DETECTION" issued Dec. 9, 2008 with Jon D. Klingensmith, Anuja Nair, Barry D. Kuban and D. Geoffrey Vince, as inventors, the teachings of which are hereby incorporated by reference herein in their entirety.

In one embodiment of the present invention, a characterization application of the IVUS system is adapted to receive and store venous characterization data (e.g., tissue type, etc.) that is subsequently utilized to classify the tissue type of a patient. For example, after a venous vessel has been interrogated (e.g., IVUS data has been collected), a histology correlation is prepared. In other words, the venous vessel is dissected or cross-sectioned for histology. In one embodiment of the present invention, the cross-section is marked, for example with one or more sutures, so that the histology can be correlated to a portion of the IVUS image based on the marker(s). The cross-section is then prepared with a fixing and staining process that is well known in the art. The staining process allows a trained clinician to identify a tissue type(s), or a chemical(s) found within (e.g., a chemical corresponding to a particular tissue type, etc.). It should be appreciated that the particular method used to identify or characterize the cross-sectional venous vessel is not a limitation of the present invention. Thus, all identification/characterization methods generally known to those skilled in the art are within the spirit and scope of the present invention.

The identified tissue type or characterization (i.e., characterization data) is then provided to the characterization application for storage and access in future procedures. Accordingly, in some instances the characterization data is stored in a venous tissue characteristic database. It should be appreciated that the data may input to the characterization application and/or database using any suitable input device(s) generally known to those skilled in the art. It should further be appreciated that the term tissue type or characterization, as these terms are used herein, include, but are not limited to, fibrous tissues, fibro-lipidic tissues, calcified necrotic tissues, calcific tissues, collagen compositions, cholesterol, thrombus, compositional structures (e.g., the lumen, the vessel wall, the medial-adventitial boundary, etc.) and all other identifiable characteristics generally known to those skilled in the art.

One method of populating the venous tissue characteristic database begins with collecting IVUS data (i.e., RF backscatter data) from a portion of a venous vessel. This data is then used to create an IVUS image at step. The interrogated portion of the venous vessel is cross-sectioned and a tissue type (or a characterization thereof) is identified. This information (i.e., characterization data) is then transmitted to a computing device (or the equivalent thereof). An image of the cross-sectioned vascular object is created and at least one region of interest is identified (e.g., by an operator). This image is then morphed, if needed, to substantially match it to the initially obtained IVUS image. This may include identifying at least one landmark and applying at least one algorithm (e.g., a morphometric algorithm, a thin plate spline deformation technique, etc.). The region(s) of interest is mapped to the IVUS image and associated IVUS data is identified. Spectral analysis is then performed on the associated IVUS data, and at least one parameter is identified. The at least one parameter and the characterization data are then stored in the database. In one embodiment of the present invention, the at least one parameter is stored such that it is linked to the characterization data. It should be appreciated that the order in which these steps are presented is not intended to limit the present invention. Thus, for example, creating an IVUS image after the vascular object is cross-sectioned is within the spirit and scope of the present invention.

The above-described process is repeated for each tissue component desired to be identified and repeated for each component as many times as desired in order to obtain a more accurate range of signal properties. With the database populated, a tissue type or characteristic can be automatically and accurately identified if the acquired parameters substantially match parameters stored in the database. With the venous tissue characteristic database populated, the characterization application of the IVUS system can then be utilized to receive IVUS data, determine parameters related thereto, and use the venous tissue characteristic parameters stored in the database (i.e., histology data) to identify tissue type(s) or characterization(s) thereof.

The central lumen 62 of the balloon catheter 52 is attached to a source of suction (not shown) at the proximal end 60 of the balloon catheter 52 by means well understood in the art. The distal end 56 of the balloon catheter 52 is advanced in the patient's vein of interest past the lesion but where the balloon 64 is downstream of the lesion. The balloon 64 is inflated so that it occludes blood flow in the vein. In this configuration, the ultimate distal end 58 is located near the lesion. The suction is activates so that suction is applied at the ultimate distal end 58. Because the ultimate distal end 58 is located in close proximity of the lesion, thrombus will be subject to the suction force and sucked into the balloon catheter to travel through the central lumen 62 to be removed through the proximal end 60.

Figure 12:
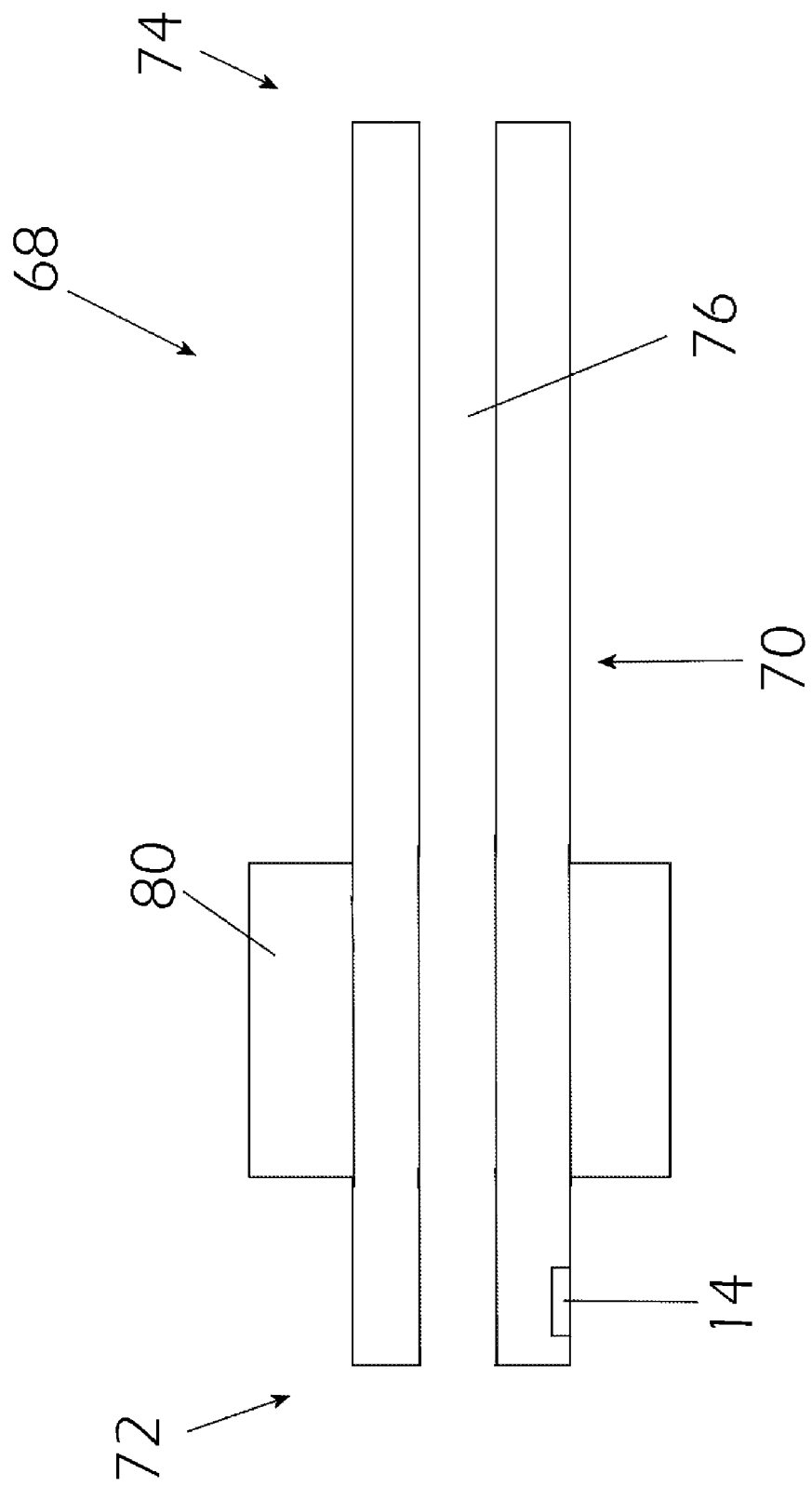
FIG. 12 is a side cross-sectional schematic view of a device of a therapy that could be applied as the therapy of the any of the therapeutic methods of the present invention.
Figure 13:
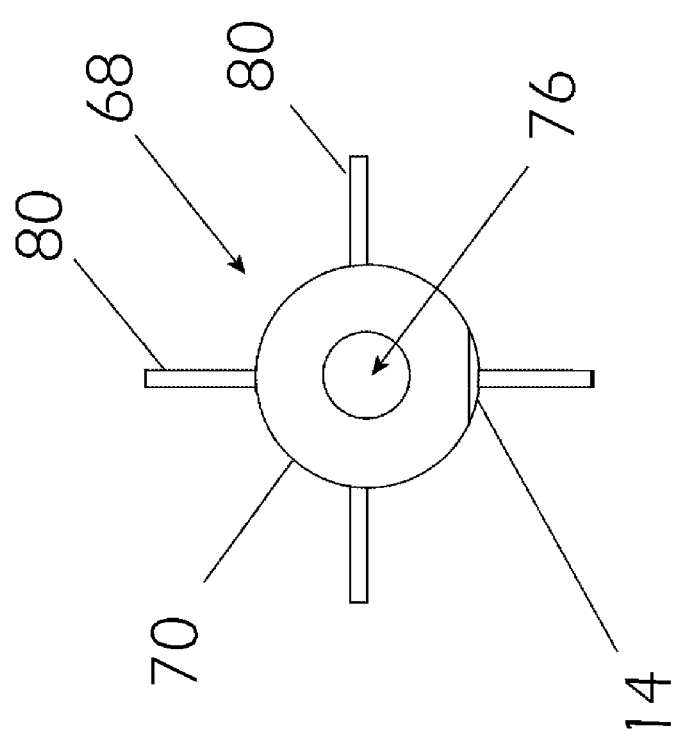
FIG. 13 is an end schematic view of the device of FIG. 12.

Another embodiment of a device of another therapy that could be applied as the therapy in step 42 is shown in FIGS. 12 and 13. In this embodiment, a cutting catheter 68 is shown. The cutting catheter 68 has a catheter body 70 with a distal end 72, a proximal end 74, a central lumen 76 through which a guide wire (not shown) may be passed and an outer surface 78. The cutting catheter 68 includes, but is not limited to, the types disclosed in U.S. Pat. No. 5,421,338 entitled "Acoustic Imaging Catheter and the Like" issued to Robert J. Crowley, Mark A. Hamm and Charles D. Lennox on Jun. 6, 1995; U.S. Pat. No. 6,283,921 entitled "Ultrasonic Visualization and Catheters Therefor" issued to Elvin Leonard Nix, Amit Kumar Som, Martin Terry Rothman and Andrew Robert Pacey on Sep. 4, 2001; U.S. Pat. No. 5,800,450 entitled "Neovascularization Catheter' issued to Banning Gray Lary and Herbert R. Radisch, Jr. on Sep. 1, 1998; U.S. Pat. Nos. 5,507,761 and 5,512,044 both entitled "Embolic Cutting Catheter" issued to Edward Y. Duer on Apr. 16, 1996 and Apr. 30, 1996, respectively; U.S. Pat. No. 5,925,055 entitled "Multimodal Rotary Abrasion and Acoustic Ablation Catheter" issued to Sorin Adrian and Paul Walinsky on Jul. 20, 1999; U.S. Pat. No. 4,917,085 entitled "Drive Cutting Catheter Having a New and Improved Motor" issued to Kevin W. Smith on Apr. 17, 1990 and US Published Patent Application No. 2006111704 entitled "Devices, Systems, and Methods for Energy Assisted Arterio-venous Fistula Creation" filed by Rodney Brenneman, Dean A. Schaefer and J. Christopher Flaherty on Nov. 16, 2005, the teachings of which are incorporated herein in their entirety by reference.

The cutting catheter 68 preferably has an imaging transducer 14 as part of an imaging system 2 located at its distal end 72. Further, the cutting catheter 68 includes cutting blades 80 located on its outer surface 78 near the distal end 72. The cutting blades 80 are preferably anywhere from about 0.5-2 mm in depth and from about 5-20 mm in length although other lengths can be used depending on the vessel that the cutting catheter 68 will be used in. The cutting blades 80 can be spaced radially around the outer surface 78 for cutting or scoring circumferentially or can be spaced on one side of the catheter 68 for selective cutting or scoring. When the catheter 68 is pulled back during an imaging procedure, the cutting blades 80 contact and score the fibrin of the lesion, particularly thrombus that is attached to and incorporated into the vein wall, thereby creating space that allows the rest of the fibrin to be compressed into a larger opening by the opening of the balloon.

Figure 14:
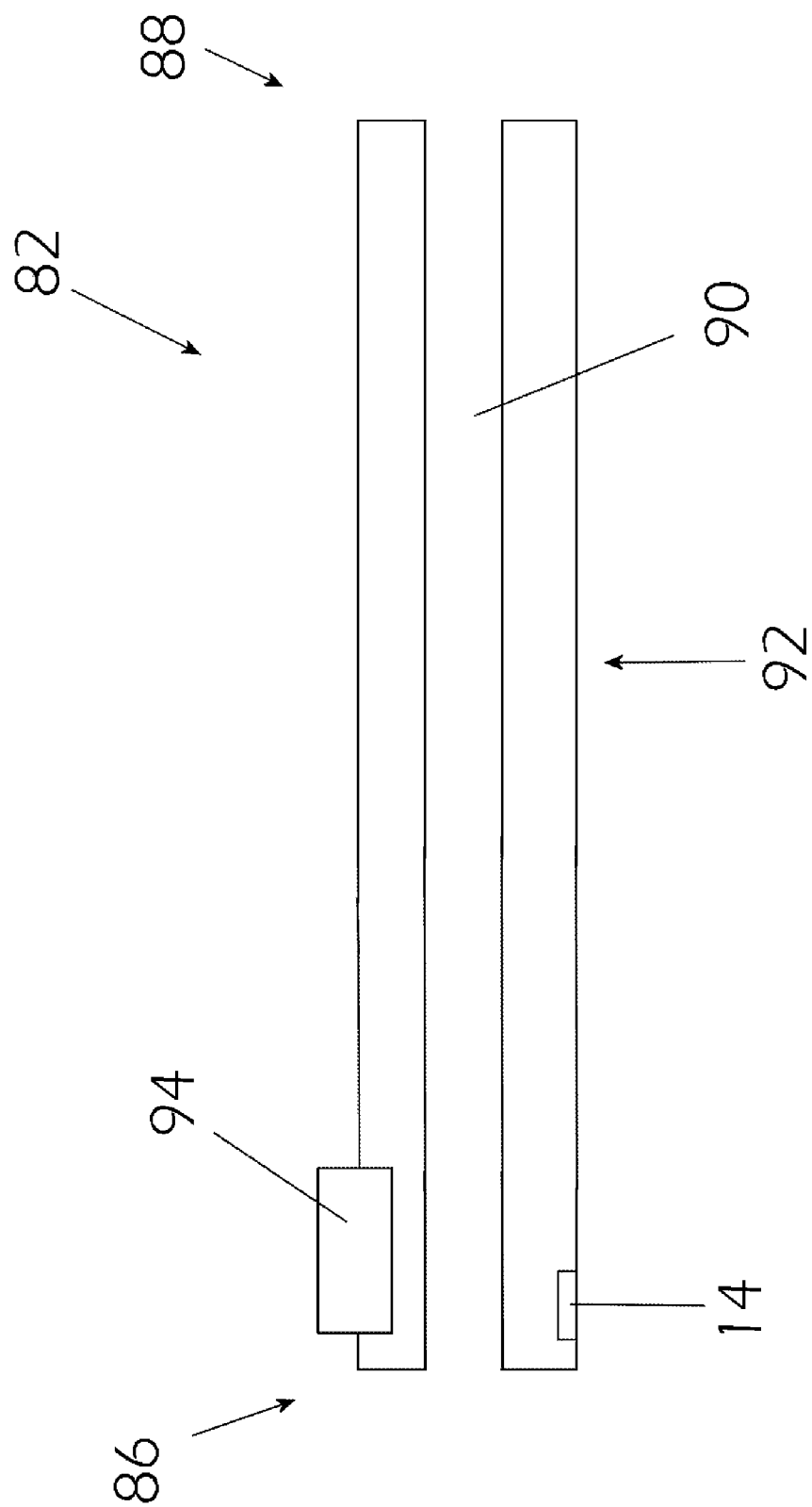
FIG. 14 is a side cross-sectional schematic view of a device of a therapy that could be applied as the therapy of the any of the therapeutic methods of the present invention.

Yet another embodiment of a device of another therapy that could be applied as the therapy in step 42 is shown in FIG. 14. In this embodiment, an ablation catheter 82 is shown. Such ablation catheter 82 delivers ablation energy through laser, so-called Radio Frequency Ablation or "RFA", both ablative and thermal, cryoablation, ultrasound, microwave or other energy sources. Examples of such ablation catheters 80 include, but are not limited to, those disclosed in U.S. Pat. No. 6,245,066 entitled "Ablation Catheter" issued to John Mark Morgan and Andrew David Cunningham on Jun. 12, 2001; U.S. Pat. No. 5,267,954 entitled "Ultra-sound catheter for removing obstructions from tubular anatomical structures such as blood vessels" issued to Henry Nita on Dec. 7, 1993; U.S. Pat. No. 6,325,797 entitled "Ablation Catheter and Method for Isolating a Pulmonary Vein" issued to Mark T. Stewart, William J. Flickinger, David E. Franscischelli, Rahul Mehra and Xiaoyi Min on Dec. 4, 2001; U.S. Pat. No. 6,203,537 entitled "Laser-driven Acoustic Ablation Catheter" issued to Sorin Adrian on Mar. 20, 2001; U.S. Pat. No. 5,427,118 entitled "Ultrasonic Guidewire" issued to John H. Wang, Henry Nita, Timothy C. Mills, and Douglas H. Gesswin on Jun. 27, 1995; U.S. Pat. No. 6,701,176 entitled "Magnetic-resonance-guided imaging, electrophysiology, and ablation" issued to Henry R. Halperin, Ronald D. Berger, Ergin Atalar, Elliot R. McVeigh, Albert Lardo, Hugh Calkins and Joao Lima on Mar. 2, 2004; U.S. Pat. No. 6,231,518 entitled "Intrapericardial electrophysiological procedures" issued to James R. Grabek, Carl M. Beaurline, Cecil C. Schmidt, Lawrence A. Lundeen and Patricia J. Rieger on May 15, 2001; U.S. Pat. No. 6,949,094 entitled "Miniature Refrigeration System for Cryothermal Ablation Catheter" issued to Ran Yaron on Sep. 27, 2005; U.S. Pat. No. 6,592,612 entitled "Method and apparatus for providing heat exchange within a catheter body" issued to Wilfred Samson, Hoa Nguyen, Mike Lee, Brady Esch, Eric Olsen and Jeff Valko on Jul. 15, 2003; U.S. Pat. No. 7,291,146 entitled "Selectable Eccentric Remodeling and/or Ablation of Atherosclerotic Material" issued to Tom A. Steinke, Corbett W. Stone, Stephen O. Ross, Brian S. Kelleher, Raphael M. Michel and Donald H. Koenig on Nov. 6, 2007; U.S. Pat. No. 7,742,795 entitled "Tuned RF energy for Selective Treatment of Atheroma and Other Target Tissues and/or Structures" issued to Corbett W. Stone, Michael F. Hoey, Tom A. Steinke, Raphael M. Michel and Arthur G. Blanck on Jun. 22, 2010; US Published Patent Application Nos. 2003092995 entitled "System and method of positioning implantable medical devices" filed by David L. Thompson on Feb. 28, 2002; 2006184048 entitled "Tissue Visualization and Manipulation System" filed by Vahid Saadat on Oct. 25, 2005; 2010256616 entitled "Recanalizing Occluded Vessels Using Radiofrequency Energy" filed by Osamu Katoh and Wayne Ogata on Apr. 2, 2010, 2008262489 entitled "Thrombus Removal" and filed by Tom A. Steinke on Apr. 23, 2008; 2008125772 entitled "Tuned RF Energy and Electrical Tissue Characterization for Selective Treatment of Target Tissues" filed by Corbett W. Stone, Michael F. Hoey, Tom A. Steinke, Raphael M. Michel, Arthur G. Blanck, Marlene Kay Truesdale and Bret Herscher on Oct. 18, 2007 and 2010125268 entitled "Selective Accumulation of Energy With or Without Knowledge of Tissue Topography" filed by Rolfe Tyson Gustus, Linas Kunstmanas and Arthur G. Blanck on Nov. 12, 2009 and WIPO Published Patent Application No. WO03073950 entitled "Optical Fibre Catheter for Thermal Ablation" filed by Andrea Venturelli on Jan. 27, 2003, the teachings of which are incorporated by reference herein in their entirety. Further examples of RF ablation systems include, but are not limited to ablative systems such as that sold by Halt Medical Inc. of Livermore, Calif. that use the heat energy of radio frequency waves to ablate tissue, those sold by Covidien plc through its Valleylab brand in Boulder, Colo. and the VNUS® RF (radiofrequency) Ablation system sold by AngioDynamics of Latham, N.Y.

The ablation catheter 82 has a catheter body 84 with a distal end 86, a proximal end 88, a central lumen 90 through which a guide wire (not shown) may be passed, an outer surface 92 and ablation system 94. The ablation catheter 82 preferably has, but is not required to have, an imaging transducer 14 as part of an imaging system 2 located at its distal end 86. As the ablation catheter 82 is advanced to the site of the lesion, the imaging system 2, if present, helps the physician to locate the lesion. Once the ablation catheter 82 is located at the lesion, the ablation therapy is applied by the ablation system 94 to ablate the lesion. The imaging system 2 may be particularly useful in helping the physician apply the ablation therapy and assess the extent of such ablation.

Figure 15:
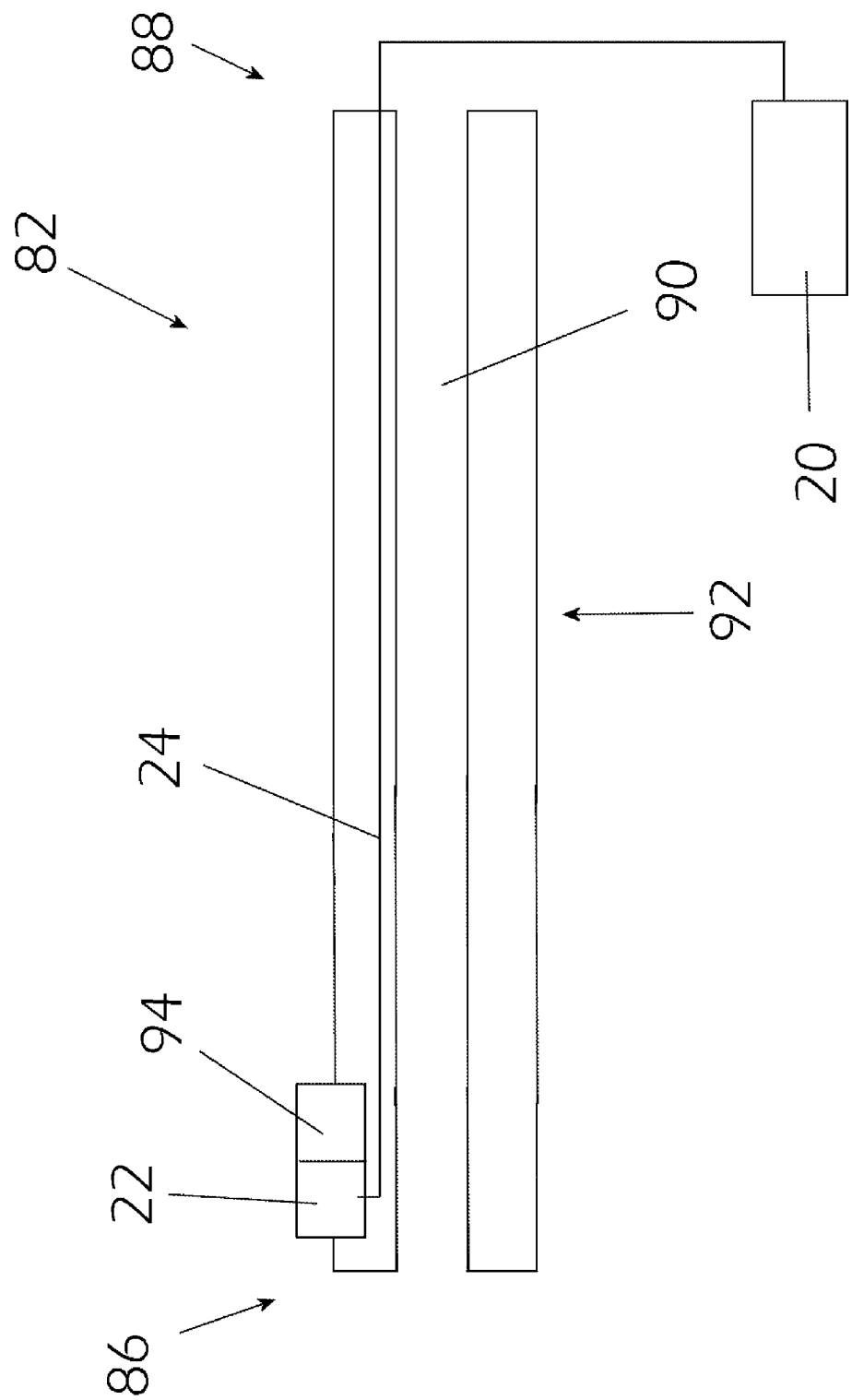
FIG. 15 is a side cross-sectional schematic view of an alternate embodiment of the device of FIG. 14.

In an alternate embodiment of the device of FIG. 14 shown in FIG. 15, the imaging system 2 is an OCT system and ablation system 94 is combined with the distal optics 22 of the imaging system 2. In a variant of this embodiment, the ablation provided by the ablation system 94 is laser ablation that is supplied to the ablation system 94 from the same light source 20 used by the OCT system to produce the OCT images, typically through optical fibers 24 connecting the light source 20 to the distal optics 22. Although the light source 20 used to produce the OCT images would typically be located remotely from the distal optics 22 supplied light via the optical fibers 24, it is within the scope of the present invention in all embodiments for the light source 20 to be located in close proximity to the distal optics 22. In a variant of this, this same light source 20 provides not only the light needed to produce the OCT images but also the laser light used by the ablation system 94 to do the ablation.

Figure 16:
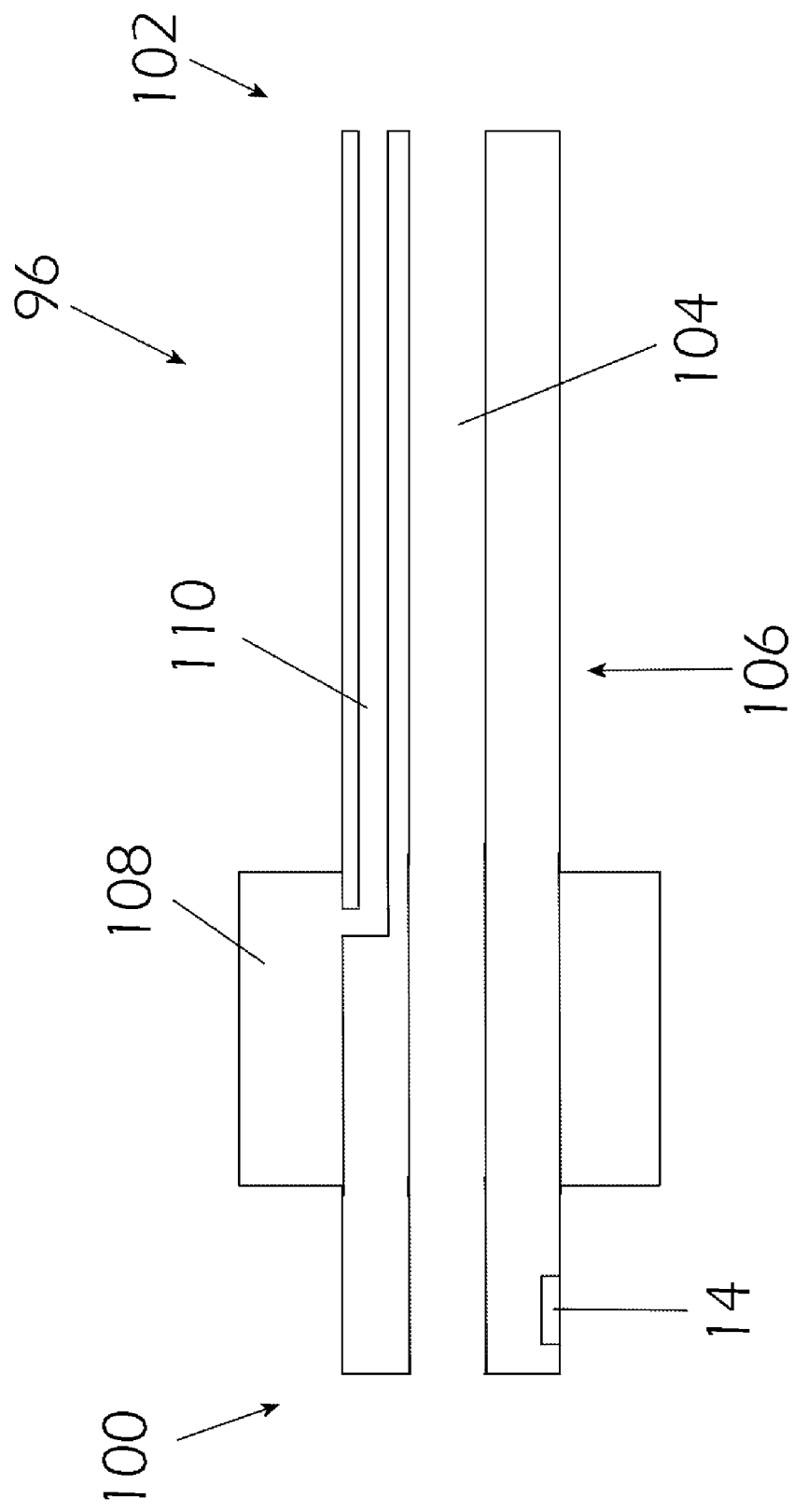
FIG. 16 is a side cross-sectional schematic view of a device of a therapy that could be applied as the therapy of any of the therapeutic methods of the present invention.

Yet another embodiment of a device of another therapy that could be applied as the therapy in step 42 is shown in FIG. 16. In this embodiment, a therapeutic agent delivery catheter 96 is shown. Such therapeutic or therapy agent delivery catheter 96 delivers a therapeutic or therapy agent to the lesion to dissolve fibrin or thrombus present at or causing the lesion or otherwise treat the lesion. Applying a therapeutic agent may increase a cross-sectional area of a lumen of a pulmonary vein. Examples of such therapeutic agent delivery catheters 96 include, but are not limited to, those disclosed in U.S. Pat. No. 5,135,516 entitled "Lubricious Antithrombogenic Catheters, Guidewires and Coatings" issued to Ronald Sahatjian and Kurt Amplatz on Aug. 4, 1992; U.S. Pat. No. 6,535,764 entitled "Gastric treatment and diagnosis device and method" issued to Mir A. Imran, Olivier K. Colliou, Ted W. Layman, Deepak R. Gandhi and Sharon L. Lake on Mar. 18, 2003; U.S. Pat. No. 5,336,178 entitled "Intravascular Catheter with Infusion Array" issued to Aaron V. Kaplan, James R. Kermode and Enrique J. Klein on Aug. 9, 1994; U.S. Pat. No. 7,063,679 entitled "Intraaortic Renal Delivery Catheter" issued to Mark Maguire and Richard Geoffrion on Jun. 20, 2006; U.S. Pat. No. 7,292,885 entitled "Mechanical Apparatus and Method for Dilating and Delivering a Therapeutic Agent to a site of Treatment" issued to Neal Scott and Jerome Segal on Nov. 6, 2007; U.S. Pat. No. 6,179,809 entitled "Drug Delivery Catheter with Tip Alignment" issued to Alexander Khairkhahan, Michael J. Horzewski, Stuart D. Harman, Richard L. Mueller and Douglas R. Murphy-Chutorian on Jan. 30, 2001; U.S. Pat. No. 5,419,777 entitled "Catheter for Injecting a Fluid or Medicine" issued to Berthold Hofling on May 30, 1995; U.S. Pat. No. 6,733,474 entitled "Catheter for Tissue dilatation and drug Delivery" issued to Richard S. Kusleika on May 11, 2004; and 2010168714 entitled "Therapeutic Agent Delivery System" filed by Jessica L. Burke, Grant T. Hoffman and Drew P. Lyons, Ellettsville, Ind. 1US) on Feb. 3, 2010; 2010125238 entitled "Iontophoretic Therapeutic Agent Delivery System" filed by Whye-Kei Lye and Kareen Looi on Nov. 7, 2009; 2003032936 entitled "Side-exit Catheter and Method for its Use" filed by Robert J. Lederman on Aug. 10, 2001, the teachings of which are incorporated by reference herein in their entirety. Examples of therapeutic agents that may be delivered to the lesion include, but are not limited to tissue plasminogen activator, urokinase, streptokinase, collagenace, hepranoids and any other fibrinolytic or direct anti-thrombin drug. The therapeutic agent delivery catheter 96 has a catheter body 98 with a distal end 100, a proximal end 102, a central lumen 104 through which a guide wire (not shown) may be passed, an outer surface 106, a balloon 108 and a balloon lumen 110. A balloon lumen may be described as an off-set lumen. The therapeutic agent delivery catheter 96 preferably has, but is not required to have, an imaging transducer 14 as part of an imaging system 2 located at its distal end 100. An imaging element or an imaging transducer may be positioned adjacent to a balloon or a therapy delivery component. The balloon 108 is inflated and deflated via the balloon lumen 110 as is well understood in the art.

The balloon 108 delivers the therapeutic agent. The balloon/off-set lumen may be configured to receive the therapeutic agent to facilitate introduction of the therapeutic agent into the balloon. The therapeutic agent may coat the balloon 108 so that as the balloon is inflated, the therapeutic agent is brought into contact with a lesion so that the therapeutic agent may be applied to the lesion. Alternately, the balloon 108 may be porous or have slits or other fenestrations to allow therapeutic agent present within the balloon to pass through the pores, slits or other fenestrations to come into contact with the tissue at or near a stenosis. The balloon of the provided treatment device may include a plurality of openings to allow a therapeutic agent contained within the balloon to be exuded from the balloon. As the therapeutic agent delivery catheter 96 is advanced to the site of the lesion, the imaging system 2, if present, helps the physician to locate the lesion. Once the therapeutic agent delivery catheter 96 is located at the lesion, the therapeutic agent to is applied to the lesion as described above. The imaging system 2 may be particularly useful in helping the physician apply the therapeutic agent and assess the extent of such therapy.

Figure 17:
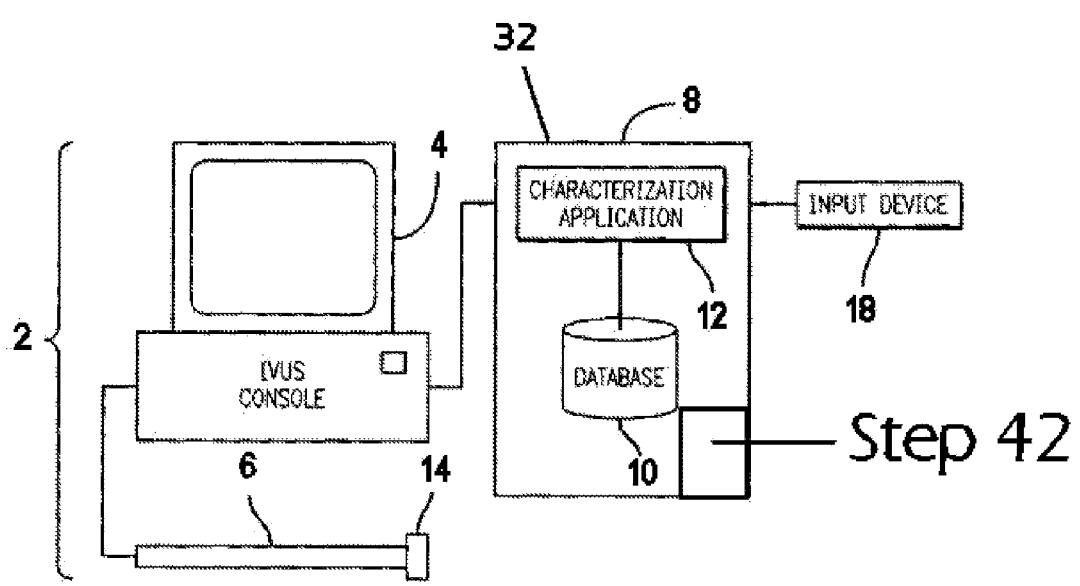
FIG. 17 is a schematic view of an embodiment of the therapeutic device of the present invention.

The therapeutic method 30 is also typically run as software on a computing device 8 and thus the combination of the computing device 8 and the therapeutic methods 24, as described above, becomes the therapeutic device 32 (FIG. 17). Although the therapeutic device 32 is preferably operated on a computing device 8, the therapeutic device 32 may also be operated separately on any system having sufficient computing capability to perform the steps of the therapeutic method 30, and diagnostic method 26 if present, and be operatively to the console 4, computing device 8, characterization application 12 or database 10 or any combination of these. In addition, the therapeutic device 32 may also be an application specific device or hardwired specifically to perform the functions described herein.

The therapeutic device 32, in preferred embodiments, acts according to algorithms described above in connection with the therapeutic method 30. The therapeutic device 32 may be implemented on or may be an adjunct to an imaging system 2. The imaging system 2 may take the form of an intravascular ultrasound (IVUS) imaging system 2 as described above including a console 4, IVUS catheter 6, a computing device 8 comprising a database 10 and a characterization application 12 electrically connected to the database 10 and typically run on the computing device 8. Alternately or in addition, the imaging system 2 may take the form of an optical coherence tomography (OCT) system that also includes a console 4, OCT catheter 6, a computing device 8 comprising a database 10 and a characterization application 12 electrically connected to the database 10 and typically run on the computing device 8.

In several embodiments of the invention described herein, the therapy delivery device 26 such as the balloon catheter 52, cutting catheter 68, ablation catheter 82 and therapeutic agent delivery catheter 96 included an imaging transducer 14 as part of an imaging system 2 that allowed the therapy delivery device to be located with respect to the lesion so that the therapy could be most effectively applied. In any of the therapy delivery systems described herein, it is preferable but not required but not required to add an imaging transducer 14 as part of an imaging system 2, typically near the distal end of such therapy delivery devices, to also allow the therapy delivery device to be located with respect to the lesion so that the therapy can be most effectively applied.

In any of the embodiments for administering a therapy described above, it may also be useful to apply embolic protection to prevent pieces of fibrin, thrombus or other tissue dislodged by the application of therapy in step 42 from moving downstream with the blood flow. Since the primary therapeutic application of the invention described herein is intended to be applied to a patient's internal jugular veins (IJV) or azygous veins (AZV), such unwanted material will move with the blood downstream into the patient's heart and ultimately into the patient's lungs where such material may cause an embolism. Consequently, the use of embolic protection such as the SPIDERFX® Embolic Protection Device made and sold by ev3, Inc. of Plymouth, Minn. and the FILTERWIRE EZ™ Embolic Protection System for SVG's made and sold by Boston Scientific, Inc. of Natick, Mass. may help prevent the occurrence of such embolisms.

Figure 18:
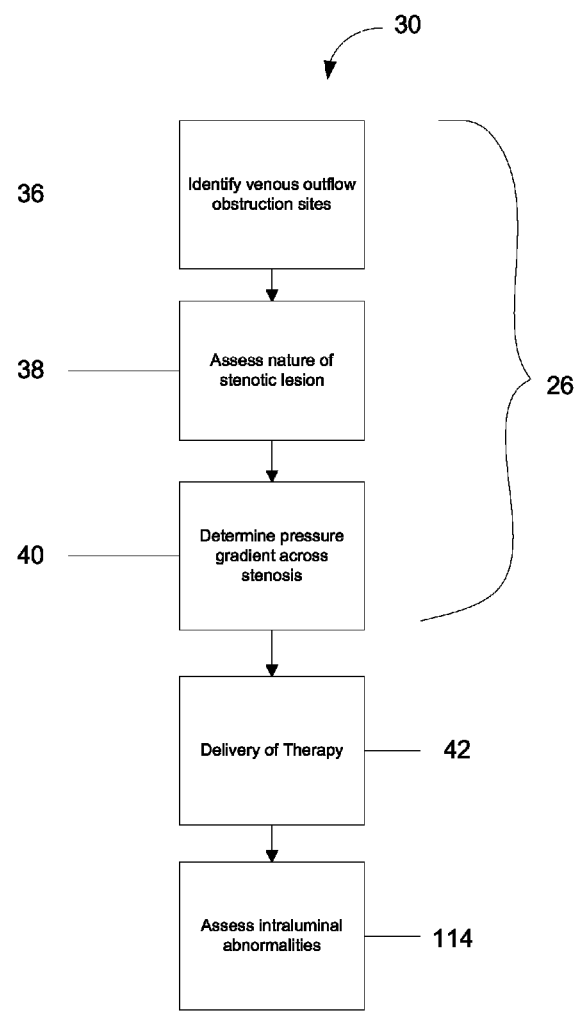
FIG. 18 is a flow chart of another embodiment of the therapeutic method of the present invention.

The therapeutic method 30 in another embodiment shown in FIG. 18 includes a step 114 so that the program passes from step 42 to step 114. In step 114, intraluminal abnormalities are assessed to see if the therapy of step 42 worked. A preferred way to assess the intraluminal abnormalities is to reintroduce the diagnostic catheter over the same exchange wire used as part of the therapy of step 42 to perform a post-therapy selective venogram and assess the residual stenosis of the lesion.

Figure 19:
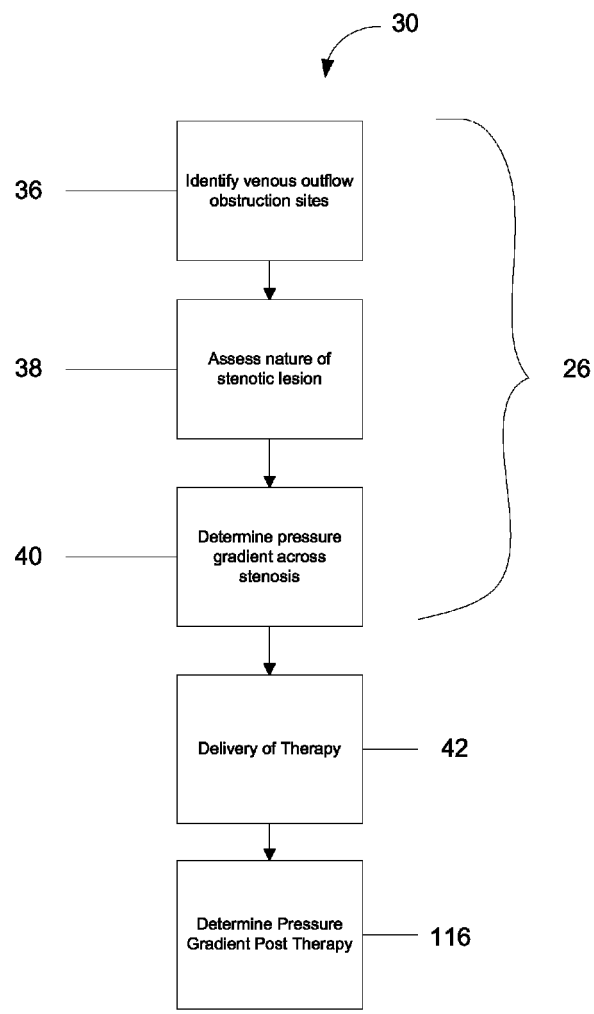
FIG. 19 is a flow chart of another embodiment of the therapeutic method of the present invention.

In a variant of all the therapeutic methods 24, as shown in FIG. 19, it is desirable to assess the pressure gradient across the stenosis after the therapy of step 42 has been applied. Consequently, after step 42 has been completed, the method passes to step 116. At step 116, the pressure gradient across the stenosis is assessed as described in step 38 to determine, post-therapy, whether adequate blood flow is now present as a result of the therapy of step 42. For example, a method may include assessing the identified venous outflow obstruction site, after applying the treatment device to the identified venous outflow obstruction site to treat pulmonary embolism symptoms of the patient, to determine the efficacy of applying the treatment device, including measuring a second pressure gradient of blood flow across the at least one venous outflow obstruction site after applying the treatment device to an identified venous outflow obstruction site.

Figure 20:
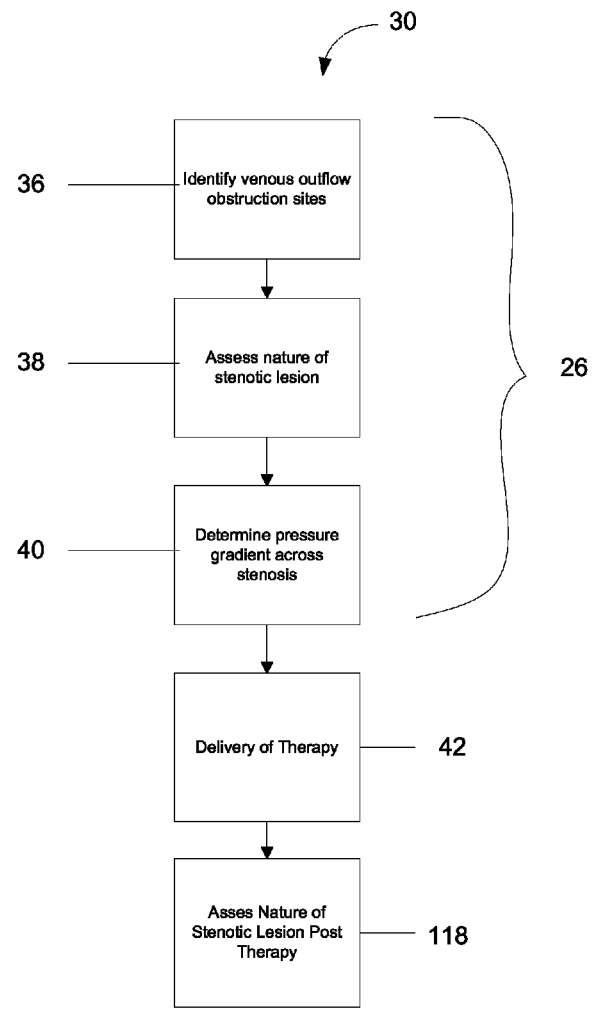
FIG. 20 is a flow chart of another embodiment of the therapeutic method of the present invention.

Further, it may be desirable to assess the nature of the stenotic lesion post-therapy. Consequently, in another embodiment of the therapeutic methods 24, as shown in FIG. 20, this assessment of the nature of the stenotic lesion post-therapy is preferably accomplished as step 118 by applying IVUS or OCT or both IVUS and OCT to the area of the applied therapy in step 42. As mentioned above, a significant stenosis is defined as luminal reduction greater than 50% of normal venous diameter as obtained during step 36 or a significant flow disruption associated with an intraluminal abnormality noted during the IVUS or OCT imaging at step 38. Consequently, a successful therapy occurs when the stenosis now has a luminal reduction less than 50% of normal venous diameter as obtained during step 36 with no significant flow disruption.

Although embodiments of the therapeutic method 30 have been described above in connection with a step 42 with may optionally include either step 116 or 118, an alternate therapeutic method 30 may also include both step 116 and 118 performed in any order.

Figure 21:
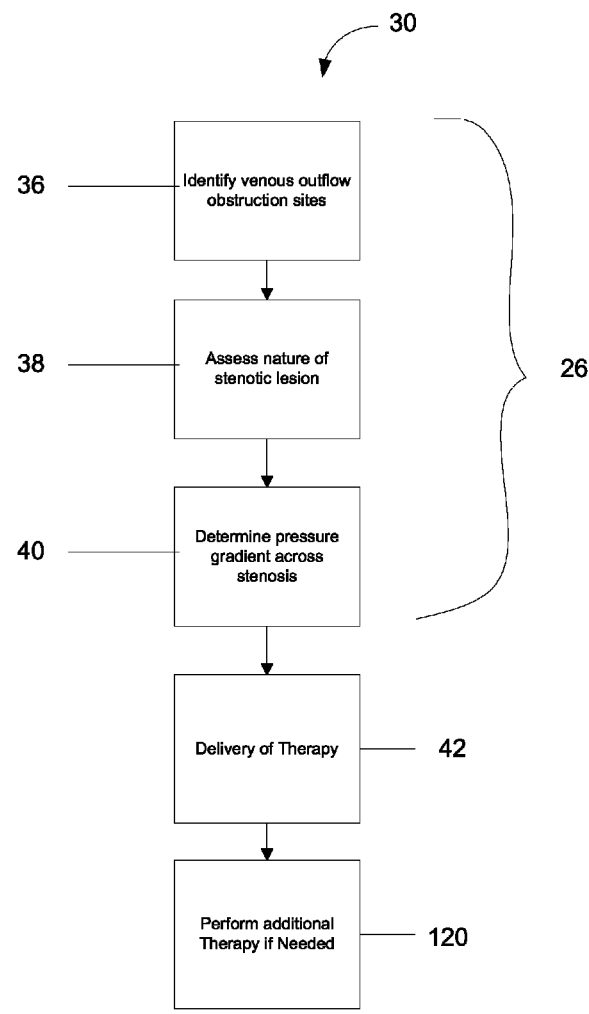
FIG. 21 is a flow chart of another embodiment of the therapeutic method of the present invention.

In addition, if the therapy of step 42 was not sufficient to provide the desired blood flow or the desired reduction of the stenosis, in an additional embodiment of the therapeutic method 30, additional therapy of any of the types described above may be applied as shown in FIG. 21. As mentioned above, the desired reduction of the stenosis is such that the residual stenosis is less than 75% of the normal proximal diameter of the stenotic vein or that a pressure gradient exceeding 1 mm Hg is no longer observed. In this embodiment of the therapeutic method 30, additional therapy will be performed if these therapy goals are not observed. Consequently, in this embodiment of the therapeutic method 30, if the therapy goals are not met, the program passes from step 42 to step 120 where step 120 is the application of an additional therapy. The therapy of step 120 may be either the reapplication of the same therapy that was applied in step 42 or the application of an entirely new therapy of the types described above. In this embodiment of the therapeutic method 30, steps 114, 116 may also be applied as described in connection with step 42 or applied singly or in combination to step 120.

Figure 22:
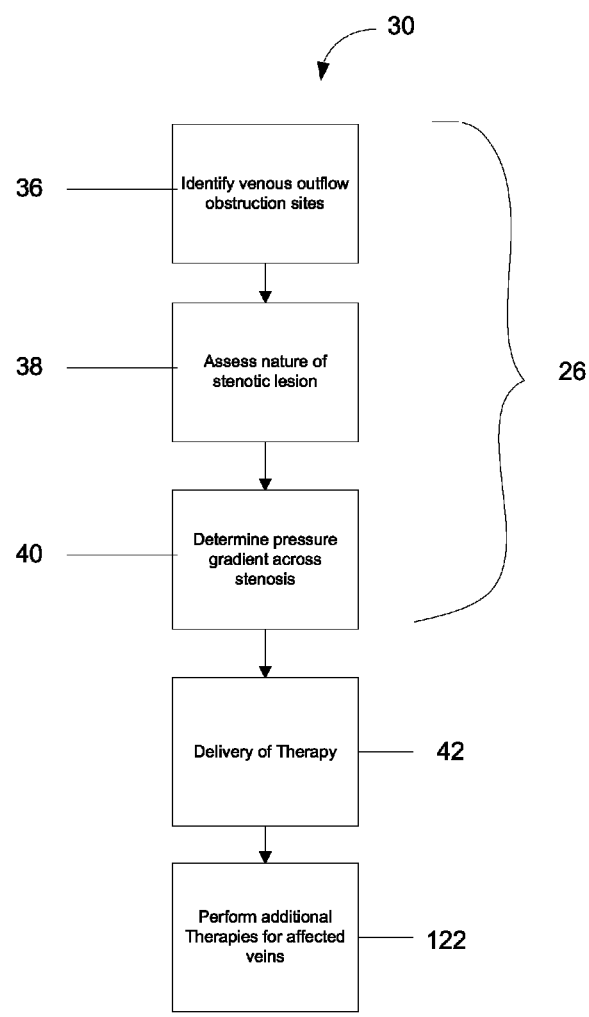
FIG. 22 is a flow chart of another embodiment of the therapeutic method of the present invention.

Further, as shown in FIG. 22, after either step 42 or step 120, additional therapy may also be performed at step 122 on all affected veins using the same techniques described above in step 42 if there are additional affected veins with significant stenoses in the IJV or AZV. Further, additional therapies or the reapplication of any of the therapies listed above in connection with steps 42 and 120 may be applied to these additional affected veins.

The present invention has been described in connection with many different diagnostic and therapeutic methods and devices. The present invention also anticipates that more than one diagnostic method and device may be applied or combined into a single method or device. Likewise, the present invention also anticipates that more than one therapeutic method and device may be applied or combined into a single method or device. Further, various permutations and combinations of diagnostic and therapeutic devices may be combined together, each acting according to the descriptions above, into a single method or single device.

Although imaging systems 2 described herein have been either intravascular ultrasound (IVUS) systems or optical coherence tomography (OCT) systems, any other system capable of producing an image of a patient's vasculature may be used as the imaging system 2. Further, although the inventions described herein have been described as being directed to primarily to the diagnosis and treatment of MS, it is also within the scope of the invention to be directed at diagnosing and treating deep vein thrombosis (DVT) and pulmonary embolisms. To diagnose and treat these maladies, the devices and methods described herein are placed in the peripheral veins or pulmonary vessels, respectively, instead of in the IJV or AZV. A pulmonary vessel may include a pulmonary vein. For these maladies, embodiments of the invention described herein that remove thrombus from the vessel wall may be particularly useful.

The present invention has been described in connection with certain embodiments, combinations, configurations and relative dimensions. It is to be understood, however, that the description given herein has been given for the purpose of explaining and illustrating the invention and are not intended to limit the scope of the invention. In addition, it is clear than an almost infinite number of minor variations to the form and function of the disclosed invention could be made and also still be within the scope of the invention. Consequently, it is not intended that the invention be limited to the specific embodiments and variants of the invention disclosed. It is to be further understood that changes and modifications to the descriptions given herein will occur to those skilled in the art. Therefore, the scope of the invention should be limited only by the scope of the claims.

What is claimed is:

1. A method of treating Pulmonary Embolism, comprising:
    providing a treatment device comprising a therapeutic agent delivery catheter capable of applying a therapeutic agent to a lesion of a pulmonary vein through the therapeutic agent delivery catheter to dissolve fibrin or thrombus present at or causing the lesion or otherwise treat the lesion, the therapeutic agent delivery catheter including an imaging element adjacent to a therapeutic delivery component, wherein the imaging element includes an ultrasound element or an optical coherence tomography (OCT) configured to image the pulmonary vein and wherein the therapeutic delivery component is configured to apply the therapeutic agent to the lesion of the pulmonary vein;
    identifying at least one venous outflow obstruction site based on images obtained from the imaging element of the therapeutic agent delivery catheter;
    assessing the at least one venous outflow obstruction site to determine whether the at least one venous outflow obstruction site causes significant narrowing of the pulmonary vein, wherein assessing the at least one venous outflow obstruction site includes measuring a first pressure gradient of blood flow across the at least one venous outflow obstruction site, and wherein the venous outflow obstruction sites causing significant narrowing of the pulmonary vein are identified for treatment with the therapeutic agent via the therapeutic agent delivery catheter;
    applying the treatment device to an identified venous outflow obstruction site of a pulmonary vein of a patient to treat pulmonary embolism symptoms of the patient, including applying the therapeutic agent to the identified venous outflow obstruction site to increase a cross-sectional area of a lumen of the pulmonary vein; and
    assessing the identified venous outflow obstruction site, after applying the treatment device to the identified venous outflow obstruction site to treat pulmonary embolism symptoms of the patient, to determine the efficacy of applying the treatment device, including measuring a second pressure gradient of blood flow across the at least one venous outflow obstruction site after applying the treatment device to an identified venous outflow obstruction site, the first and second pressure gradients being pressure differentials of a pressure distal to the at least one venous outflow obstruction site of the pulmonary vein and a pressure in the superior vena cava.

2. The method of claim 1, wherein the therapeutic agent delivery catheter has a catheter body with a distal end, a proximal end, a central lumen through which a guide wire may be passed, an outer surface, a balloon and a balloon lumen.

3. The method of claim 2, wherein applying the treatment device to the identified venous outflow obstruction site of the vessel includes visualizing the identified venous outflow obstruction site with the imaging element.

4. The method of claim 2, wherein the balloon of the provided treatment device is coated with the therapeutic agent chosen from the group consisting of tissue plasminogen activator, urokinase, streptokinase, collagenace, hepranoids and any other fibrinolytic or direct anti-thrombin drug so that as the balloon is inflated, the therapeutic agent is brought into contact with a lesion so that the therapeutic agent may be applied to the lesion.

5. The method of claim 2, wherein the balloon of the provided treatment device is porous to a therapeutic agent to allow the therapeutic agent contained within the balloon to be exuded from the balloon.

6. The method of claim 5, wherein the therapeutic agent is chosen from the group consisting of tissue plasminogen activator, urokinase, streptokinase, collagenace, hepranoids and any other fibrinolytic or direct anti-thrombin drug.

7. The method of claim 6, wherein the balloon lumen of the catheter of the provided treatment device is configured to receive the therapeutic agent to facilitate introduction of the therapeutic agent into the balloon.

8. The method of claim 2, wherein the balloon of the provided treatment device includes a plurality of openings to allow a therapeutic agent contained within the balloon to be exuded from the balloon.

9. The method of claim 8, wherein the therapeutic agent is chosen from the group consisting of tissue plasminogen activator, urokinase, streptokinase, collagenace, hepranoids and any other fibrinolytic or direct anti-thrombin drug.

10. The method of claim 9, wherein the balloon lumen of the catheter of the provided treatment device is configured to receive the therapeutic agent to facilitate introduction of the therapeutic agent into the balloon.

11. A Pulmonary Embolism therapeutic method, comprising:
    providing a treatment device that includes:
        a catheter having a proximal portion, a distal portion, a central lumen extending along a length of the catheter between the proximal and distal portions, and an off-set lumen extending along the length of the catheter between the proximal and distal portions; and
        a balloon coupled to the distal portion of the catheter such that the balloon is in fluid communication with the off-set lumen of the catheter such that a therapeutic agent can be introduced into the balloon through the off-set lumen, wherein the therapeutic agent is configured to dissolve fibrin or thrombus present at a lesion of a pulmonary vein and wherein the balloon is configured to facilitate application of the therapeutic agent from the balloon to the lesion when the balloon is positioned adjacent the lesion; and
        an imaging element positioned adjacent to the balloon, wherein the imaging element includes an ultrasound element or an optical coherence tomography (OCT) element configured to image the pulmonary vein;
    identifying at least one venous outflow obstruction site based on images obtained from the imaging element;
    assessing the at least one venous outflow obstruction site to determine whether the at least one venous outflow obstruction site causes significant narrowing of the pulmonary vein, wherein assessing the at least one venous outflow obstruction site includes measuring a first pressure gradient of blood flow across the at least one venous outflow obstruction site, and wherein the venous outflow obstruction sites causing significant narrowing of the pulmonary vein are identified for treatment with the therapeutic agent via the treatment device;

applying the treatment device to an identified venous outflow obstruction site of a pulmonary vein of a patient to treat pulmonary embolism symptoms of the patient, including inflating the balloon adjacent to the identified venous outflow obstruction site to apply the therapeutic agent to the identified venous outflow obstruction site to increase a cross-sectional area of a lumen of the pulmonary vein; and evaluating the efficacy of applying the treatment device to the identified venous outflow obstruction site to treat pulmonary embolism symptoms of the patient, after applying the treatment device, including measuring a second pressure gradient of blood flow across the at least one venous outflow obstruction site after applying the treatment device to the identified venous outflow obstruction site, the first and second pressure gradients being pressure differentials of a pressure distal to the at least one venous outflow obstruction site of the pulmonary vein and a pressure in the superior vena cava.

12. The method of claim 11, wherein the central lumen of the catheter of the provided treatment device is sized and shaped to receive a guidewire.

13. The method of claim 12, wherein the balloon of the provided treatment device includes a plurality of openings to allow a therapeutic agent contained within the balloon to be exuded from the balloon.

14. The method of claim 13, wherein the therapeutic agent is chosen from the group consisting of tissue plasminogen activator, urokinase, streptokinase, collagenace, hepranoids and any other fibrinolytic or direct anti-thrombin drug.

15. The method of claim 14, wherein the off-set lumen of the catheter of the provided treatment device is configured to receive the therapeutic agent to facilitate introduction of the therapeutic agent into the balloon.

16. The method of claim 11, wherein applying the treatment device to the identified venous outflow obstruction site of the vessel includes visualizing the identified venous outflow obstruction site with the imaging element.

17. The method of claim 11, wherein the balloon of the provided treatment device is coated with the therapeutic agent chosen from the group consisting of tissue plasminogen activator, urokinase, streptokinase, collagenace, hepranoids and any other fibrinolytic or direct anti-thrombin drug so that as the balloon is inflated, the therapeutic agent is brought into contact with a lesion so that the therapeutic agent may be applied to the lesion.

18. The method of claim 11, wherein the balloon of the provided treatment device is porous to the therapeutic agent to allow the therapeutic agent contained within the balloon to be exuded from the balloon.

19. The method of claim 18, wherein the therapeutic agent is chosen from the group consisting of tissue plasminogen activator, urokinase, streptokinase, collagenace, hepranoids and any other fibrinolytic or direct anti-thrombin drug.

20. The method of claim 19, wherein the off-set lumen of the catheter of the provided treatment device is configured to receive the therapeutic agent to facilitate introduction of the therapeutic agent into the balloon.

* * * * *